US010204707B2

(12) United States Patent
Pestian et al.

(10) Patent No.: US 10,204,707 B2
(45) Date of Patent: Feb. 12, 2019

(54) COMPUTER IMPLEMENTED SYSTEM AND METHOD FOR ASSESSING A NEUROPSYCHIATRIC CONDITION OF A HUMAN SUBJECT

(75) Inventors: John Pestian, Cincinnati, OH (US); Tracy A. Glauser, Cincinnati, OH (US); Bruce Aronow, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 447 days.

(21) Appl. No.: 13/266,272

(22) PCT Filed: Apr. 27, 2010

(86) PCT No.: PCT/US2010/032513
§ 371 (c)(1),
(2), (4) Date: Oct. 26, 2011

(87) PCT Pub. No.: WO2010/126867
PCT Pub. Date: Nov. 4, 2010

(65) Prior Publication Data
US 2012/0041911 A1   Feb. 16, 2012

Related U.S. Application Data

(60) Provisional application No. 61/214,707, filed on Apr. 27, 2009.

(51) Int. Cl.
*G06N 99/00* (2010.01)
*G16H 50/30* (2018.01)
(Continued)

(52) U.S. Cl.
CPC ............. *G16H 50/20* (2018.01); *G06F 19/00* (2013.01); *G06N 99/005* (2013.01); *G16H 50/30* (2018.01)

(58) Field of Classification Search
CPC ...... G06N 99/005; G16H 50/20; G16H 50/30; G06F 19/00
See application file for complete search history.

(56) References Cited

U.S. PATENT DOCUMENTS 6,076,088 A   6/2000   Paik et al.
8,145,716 B2  3/2012   Karamchedu et al.
(Continued)

OTHER PUBLICATIONS

Chandler, Lalonde, Sokol, Hallett, "Personal Persistence, Identity Development, and Suicide: A Study of Native and Non-Native North American Adolescents" In press, Monographs of the Society for Research in Child Development, Apr. 2003, pp. 1-75.*
(Continued)

*Primary Examiner* — Kakali Chaki
*Assistant Examiner* — Eric Nilsson
(74) *Attorney, Agent, or Firm* — Mintz Levin Cohn Ferris Glovsky and Popeo, P.C.; Muriel Liberto, Esq.

(57) ABSTRACT

A method for assessing a neuropsychiatric condition (such as, but not limited to, a risk that a subject may attempt to commit suicide or repeat an attempt to commit suicide, a risk that terminally ill patient is not being care-for or treated according to the patient's true wishes, a risk that a subject may perform or repeat a criminal act and/or a harmful act, a risk of the subject having a psychiatric illness, and/or a risk of a subject feigning a psychiatric illness) may include a plurality of steps. A step may include receiving biomarker data associated from an analysis of the subject's biological sample and a step of receiving thought-marker data obtained pertaining to one or more of the subject's recorded thoughts, spoken words, transcribed speech, and writings. A step may include generating a biomarker score associated with the neuropsychiatric condition from the biomarker data. A step may include generating a thought-marker score associated with the neuropsychiatric condition from the thought-
(Continued)

marker data. And a step may involve calculating a neuropsychiatric condition score based, at least in part, upon the biomarker score and the thought-marker score. Such method may be operating from one or more memory devices including computer-readable instructions configured to instruct a computerized system to perform the method, and the method may be operating on a computerized system including one or more computer servers (or other available devices) accessible over a computer network such as the Internet or over some other data network.

17 Claims, 7 Drawing Sheets

(51) Int. Cl.
G16H 50/20 (2018.01)
G06F 19/00 (2018.01)

(56) References Cited

U.S. PATENT DOCUMENTS

| | | | |
|---|---|---|---|
| 2002/0046259 A1 | 4/2002 | Glorikian | |
| 2003/0199740 A1 | 10/2003 | Iliff | |
| 2003/0217335 A1 | 11/2003 | Chung et al. | |
| 2004/0024293 A1 | 2/2004 | Lawrence et al. | |
| 2004/0054744 A1 | 3/2004 | Karamchedu et al. | |
| 2005/0037405 A1 | 2/2005 | Caspi et al. | |
| 2005/0069936 A1* | 3/2005 | Diamond | A61K 31/00 435/6.16 |
| 2006/0092920 A1 | 5/2006 | Karamchedu et al. | |
| 2006/0129383 A1* | 6/2006 | Oberlander et al. | 704/10 |
| 2007/0065821 A1 | 3/2007 | Kudaravalli et al. | |
| 2007/0213981 A1* | 9/2007 | Meyerhoff et al. | 704/243 |
| 2007/0224599 A1 | 9/2007 | Kendler | |
| 2007/0294113 A1 | 12/2007 | Settimi | |
| 2009/0006001 A1 | 1/2009 | Niculescu, III et al. | |
| 2010/0273153 A1* | 10/2010 | Tabakoff et al. | 435/6 |

OTHER PUBLICATIONS

Mossner, Mikova, Koutsilieri, Saoud, Ehlis, Muller, Fallgatter and Riederer, "Consensus Paper of the WFSBP Task Force on Biological Markers: Biological Markers in Depression", The World Journal of Biological Psychiatry, col. 8(3), 2007, pp. 141-174.*
Shen, Olbrich, Achermann, Meier, "Dimensional Complexity and Spectral Properties of the Human Sleep EEG", Clkinical Neurophysiology, vol. 114, 2003, pp. 199-209.*
Robin, Turck, Hainard, Lisacek, Sanchez, Muller, "Bioinformatics for Protein Biomarker Panel Classification: What is needed to bring Biomarker Panels into in vitro Diagnostics", Expert Rev Proteomics, 6(6), Dec. 2009, pp. 675-689.*
Reynolds, Mazza, "Assessment of Suicidal Ideation in Inner-City Children and Young Adolescents: Reliability and Validity of the Suicidal Ideation Questionnaire-JR", School Psychology Review, vol. 28, No. 1, 1999, pp. 17-30.*
Liu, Li, Qin, et al., "Association of TPH1 with Suicidal Behaviour and Psychiatric Disorders in the Chinese Population", Journal of Medical Genetics, vol. 43: E04, 2006, pp. 1-6.*
Williams, "The Relationship among Linguistic Patterns, Thwarted Belongingness, Perceived Burdensomeness, and Suicidal Behavior: A Test of Joiner's Theory of Suicide", phD Thesis, published by Florida State University, Florida, USA, 2006, pp. 1-103.*
Tawanda Carleton Sibanda, "Was the Patient Cured? Understanding Semantic Categories and Their Relationships in Patient Records", Master's of Engineering Thesis published by Department of Electrical Engineering and Computer Science at Massachusetts Institute of Technology, Jun. 2006, pp. 1-107.*
Victoria Arango, Yung-yu Huang, Mark D. Underwood, J. John Mann, "Genetics of the serotonergic system in suicidal behavior", Journal of Psychiatric Research, vol. 37, 2003, pp. 375-386.*

B. Bondy, A. Buettner and P. Zill, "Genetics of Suicide", Molecular Psychiatry, vol. 11, 2006, pp. 336-351.*
Aaron T. Beck, Maria Kovacs, Arlene Weissman, "Assessment of Suicidal Intention: The Scale for Suicide Ideation", Journal of Consulting and Clinical Psychology, vol. 47, No. 2, 1979, pp. 343-352.*
Trevor Cohen, Brett Blatter, Vimla Patel, "Simulating expert clinical comprehension: Adapting latent semantic analysis to accurately extract clinical concepts from psychiatric narrative", Journal of Biomedical Informatics, vol. 41, 2008, pp. 1070-1087.*
J. John Manna et al. "Candidate Endophenotypes for Genetic Studies of Suicidal Behavior", Biol Psychiatry, vol. 65(7), Apr. 1, 2009, pp. 556-563.*
Theodore P. Beauchaine, Emily Neuhaus, Sharon L. Brenner, Lisa Gatzkekopp, "Gen Good Reasons to Consider Biological Processes in Prevention and Intervention Research", Dev Psychopathol, vol. 20(3), 2008, pp. 745-774.*
Francesca Mallamaci, Giovanni Tripepi, Sebastiano Cutrupi, Lorenzo S. Malatino, Carmine Zoccali, Prognaostic Value of Combined Use of Biomarkers of Inflammation, Endothelal Dysfunction, and Myocardiopathy in Patients with ESRD, Kidney International, vol. 67, 2005, pp. 2330-2337.*
Barak, Azy, et al, "Writing Characteristics of Suicidal People on the Internet: A Psychological Investigation of Emerging Social Environments," Suicide and Life-Threatening Behavior, The American Association of Suicidology, Oct. 2005, vol. 35, No. 5, pp. 507-524, Washington DC, USA.*
Pennebaker, James W., Matthias R. Mehl, and Kate G. Niederhoffer. "Psychological aspects of natural language use: Our words, our selves." Annual review of psychology 54.1 (2003): 547-577.*
Arango, Victoria, et al. "Genetics of the serotonergic system in suicidal behavior." Journal of psychiatric research 37.5 (2003): 375-386.*
Final rejection in U.S. Appl. No. 12/006,813, filed Jan. 4, 2008, dated Oct. 12, 2012.
Rada, et al., Development and Application of a Metric on Semantic Nets, IEEE Transaction on Systems, Man, and Cybernetics, pp. 17-30, Jan./Feb. 1989, vol. 19, No. 1, IEEE, New York City, New York, US.
Bluebond-Langner, Myra, et al., "Children's Views of Death", Oxford Textbook of Palliative Care, 2005, pp. 85-94; Oxford University Press, New York, USA. [Month of publication is unknown. The year of publication is sufficiently earlier than the effective U.S. filling date and any foreign priority date so the particular month of publication is not in issue.].
Zethelius, Bjorn, et al., "Use of Multiple Biomarkers to Improve the Prediction of Death from Cardiovascular Cures," The New England Journal of Medicine, May 15, 2008, vol. 358, No. 20, pp. 2107-2116, Massachusetts Medical Society, Boston, Massachusetts, USA.
Clarke, Robert, et al., "Biomarkers of Inflammation Predict Both Vascular and Non-Vascular Mortality in Older Men," European Heart Journal, Jan. 16, 2008, Issue 29, pp. 800-809, European Society of Cardiology, Sophia Antipolis, France.
Mishra, Jaya, et al, "Neutrophil gelatinase-associated lipocalin (NGAL) as a biomarker for acute renal injury afer cardiac surgery," The Lancet, Apr. 2, 2005, vol. 365, pp. 1231-1238, New York, New York, USA.
Gronroos, Marika H., et al., "Comparison of glomerular function tests in children with cancer," Pediatr Nephrol, Jan. 23, 2008, vol. 23, pp. 797-803, International Pediatrics Nephrology Association, Springer, Los Angeles, California, USA.
Shilpak, Michael G., et al., "Cystatin C and the Risk of Death and Cardiovascular Events among Elderly Persons," The New England Journal of Medicine, May 19, 2005, vol. 352, No. 20, pp. 2049-2060, Massachusetts Medical Society, Boston, Massachusetts, USA.
World Health Organization, "WHO definition of Pallative Care," 2009 [cited Nov. 10, 2009][date retrieved Feb. 13, 2013](available from http://www.who.int/cancer/pallative/definition).
O'Connor, Rory C., et al, "A Thematic Analysis of Suicide Notes," Crisis, The Journal of Crisis Intervention and Suicide Prevention, May-Jun. 1999, vol. 20, No. 3, pp. 106-114, Hogrefe & Huber Publishers, Boston, Massachusetts, USA.

(56) References Cited

OTHER PUBLICATIONS

Innamorati, Marco, et al., "Completed Versus Attempted Suicide in Psychiatric Patients: A Psychological Autopsy Study," Journal of Psychiatric Practice, Jul. 2008, vol. 14, No. 4, pp. 216-224, Lippincott Williams & Wilkins, New York, New York, USA.

Jones, Natalie J., et al., "The Development and Validation of Statistical Prediction Rules for Discriminating Between Genuine and Simulated Suicide Notes," Archives of Suicide Research, International Academy for Suicide Research, Mar. 2007, vol. 11, pp. 219-233, Routledge Taylor & Francis Group, Florence, Kentucky, USA.

Handelman, Lori D., et al., "The Content of Suicide Notes from Attempters and Completers," Crisis, 2007, vol. 28, No. 2, pp. 102-104, Hogrefe & Huber Publishers, Boston, Massachusetts, USA. [Month of publication is unknown. The year of publication is sufficiently earlier than the effective U.S. filling date and any foreign priority date so the particular month of publication is not in issue.].

Foster, Tom, "Suicide Note Themes and Suicide Prevention," International Journal of Psychiatry in Medicine, 2003, vol. 33, No. 4, pp. 323-331, Baywood Publishing Company, Inc., Amityville, New York, USA. [Month of publication is unknown. The year of publication is sufficiently earlier than the effective U.S. filling date and any foreign priority date so the particular month of publication is not in issue.].

Demirel, Birol, et al., "Farewell to the World: Suicide Notes from Turkey," Suicide and Life-Threatening Behavior, Feb. 2008, vol. 38, No. 1, pp. 122-127, The American Association of Suicidology, Washington DC, USA.

Chavez-Hernandez, Ana-Maria, et al., "Suicide notes from Mexico and the United States: a thematic analysis," Salud Publica de Mexico, Jul.-Aug. 2009, vol. 51, No. 4, pp. 314-320 Guanajuato, Mexico.

Leenaares, Antoon A., et al., "A Predictive Approach to the Study of Manifest Content in Suicide Notes," Journal of Clinical Psychology, Jan. 1981, vol. 37, No. 1, pp. 50-52, Wiley-Blackwell, Hoboken, New Jersey, USA.

Frederick, Christina M., et al., "A Mediational Model of Social Physique Anxiety and Eating Disordered Behaviors," Perceptual and Motor Skills, Dec. 1997, vol. 86, pp. 139-145, Ammons Scientific, Missoula, Montana, USA.

Brummett et al. "Effects of Environmental Stress and Gender on Associations Among Symptoms of Depression and the Serotonin Transporter Gene Linked Polymorphic Regions (5-HTTLPR)." *Behav. Genet.* 38.1(2007):34-43.

Non-Final Office action, U.S. Appl. No. 12/006,813, filed Jan. 4, 2008, dated Dec. 19, 2013, 24 pgs., United States Patent & Trademark Office, Alexandria, Virginia, USA.

\* cited by examiner ated with the neuropsychiatric condition from the biomarker data. A step may include generating a thought-marker score associated with the neuropsychiatric condition from the thought-marker data. And a step may involve calculating a neuropsychiatric condition score based, at least in part, upon the biomarker score and the thought-marker score. As will be appreciated, many of these steps do not necessarily need to be performed in the order provided and some of the steps may be combined into a single step or operation.

COMPUTER IMPLEMENTED SYSTEM AND METHOD FOR ASSESSING A NEUROPSYCHIATRIC CONDITION OF A HUMAN SUBJECT

CROSS-REFERENCE TO RELATED APPLICATIONS

This application is a national state entry of PCT/US2010/032513, filed Apr. 27, 2010, which claims the benefit of the U.S. Provisional App. Ser. No. 61/214,707, filed Apr. 27, 2009, both of which are incorporated herein by reference.

BACKGROUND

There is a need for more accurate assessment of human subject's neuropsychiatric conditions so that the human subject may be better treated for such conditions by their caregivers. For example, there are needs for better assessment of a suicide risk in an individual, there are needs for better assessment of end-of-life treatment care for terminally ill patients, there are needs for better assessment and treatment of schizophrenic patients, there are needs for better assessment and handling of a criminal act (or repeat criminal act) attempt risk for an individual, there are needs for better assessment and treatment of other neuropsychiatric conditions, and there are needs for better assessment and handling of those feigning neuropsychiatric conditions.

With respect to suicide risk, it is estimated that each year 800,000 people die by suicide worldwide. In the United States alone, eighty people kill themselves each day, twelve under the age 25. Experts estimate the total life time costs of suicide to be $33 billion. The Centers for Disease Control and Prevention, however, notes that approximately 15% of all high-school students have developed a serious plan to attempt suicide, 9% have attempted suicide, and nearly 3% have required medical attention due to a suicide attempt. In an average year, a typical pediatric emergency department evaluates at least 2,000 patients exhibiting suicidal behavior. A challenge for those who care for suicide attempters may be assessing the likelihood of another serious suicide attempt, which may be lethal.

With respect to end-of-life treatment and care of terminally ill subjects, One option is to support a clinical atmosphere that understands when death is certain, and knows when to shift from life saving medical care to preparing for the inevitable, death. In the later case, establishing expectations and providing specialized end-of-life care becomes the norm. With children, especially, understanding the dying child's concerns can be difficult. These children may be anxious about pain and discomfort, they may struggle with what will happen to them when they die, or they may worry about making family members sad, they may feel alone, stupid, or angry. As care providers understand the dying child's concerns they can better provide personalized care to the child and family.

SUMMARY

A method for assessing a neuropsychiatric condition (such as, but not limited to, a risk that a subject may attempt to commit suicide or repeat an attempt to commit suicide, a risk that terminally ill patient is not being care-for or treated according to the patient's true wishes, a risk that a subject may perform or repeat a criminal act and/or a harmful act, a risk of the subject having a psychiatric illness, and/or a risk of a subject feigning a psychiatric illness) may be provided. Such method may be operating from one or more memory devices including computer-readable instructions configured to instruct a computerized system to perform the method, and the method may be operating on a computerized system including one or more computer servers (or other available devices) accessible over a computer network such as the Internet or over some other data network. The method may include a plurality of steps. A step may include receiving biomarker data associated from an analysis of the subject's biological sample and a step of receiving thought-marker data obtained pertaining to one or more of the subject's recorded thoughts, spoken words, transcribed speech, and writings. A step may include generating a biomarker score associ- In an embodiment, the step of generating the biomarker score may include a step of assessing a level of at least a cytokine, a metabolite, a polymorphism, a genotype, a polypeptide, and an mRNA of the human subject. For example, the step of generating the biomarker score may include a step of assessing a level of a hydroxyindoleaceticacid (5HIAA).

In an embodiment, the step of generating a thought-marker score includes a step of determining a correlation between (a) the human subject's recorded thoughts, spoken words, transcribed speech and/or writings; and (b) a corpus of thought data collected pertaining, at least in part, to the neuropsychiatric condition. Further, this correlation may be determined, at least in part, utilizing natural language processing and/or machine learning algorithms.

In an embodiment, the method may further include a step of receiving clinical data of the subject associated with the neuropsychiatric condition; may include a step of generating a clinical data score from the clinical data; and the step of calculating in neuropsychiatric condition score may be based, at least in further part, upon the clinical data score. Further, the clinical data of the subject associated with the neuropsychiatric condition may include at least a portion of medical patient record data associated with the subject; may include demographic data associated with the subject; and/or may include interview and/or survey data obtained from the subject. With this embodiment, it is possible that the step of calculating a neuropsychiatric condition score may include steps of (a) normalizing the biomarker score, (b) normalizing the thought-marker score, (c) normalizing the clinical data score and (d) calculating a mean of at least the normalized biomarker, thought marker and clinical data scores. Further, the normalizing steps normalize between a numerical scale of 0.0 to 1.0 and/or a scale of 0 and $10^N$, wherein N is an integer. Further, the step of generating a clinical data score may include a step of calculating a percentage of risks associated with the neuropsychiatric condition from the subject compared to a predetermined set of risks associated with the neuropsychiatric condition.

In an embodiment, the step of generating a biomarker score includes a step of calculating a composite score related to two or more biological markers associated with the neuropsychiatric condition from the biomarker data.

In an embodiment, the step of calculating a neuropsychiatric condition score includes steps of (a) normalizing the biomarker score, (b) normalizing the thought marker score and (c) calculating a mean of at least the normalized biomarker and the thought marker scores.

In an embodiment, the method further includes a step of automatically recommending, based upon the calculated neuropsychiatric condition score, a subject's treatment regimen, a subject's counseling session, a subject's intervention program and/or a subject's care program.

DETAILED DESCRIPTION

Figure 1:
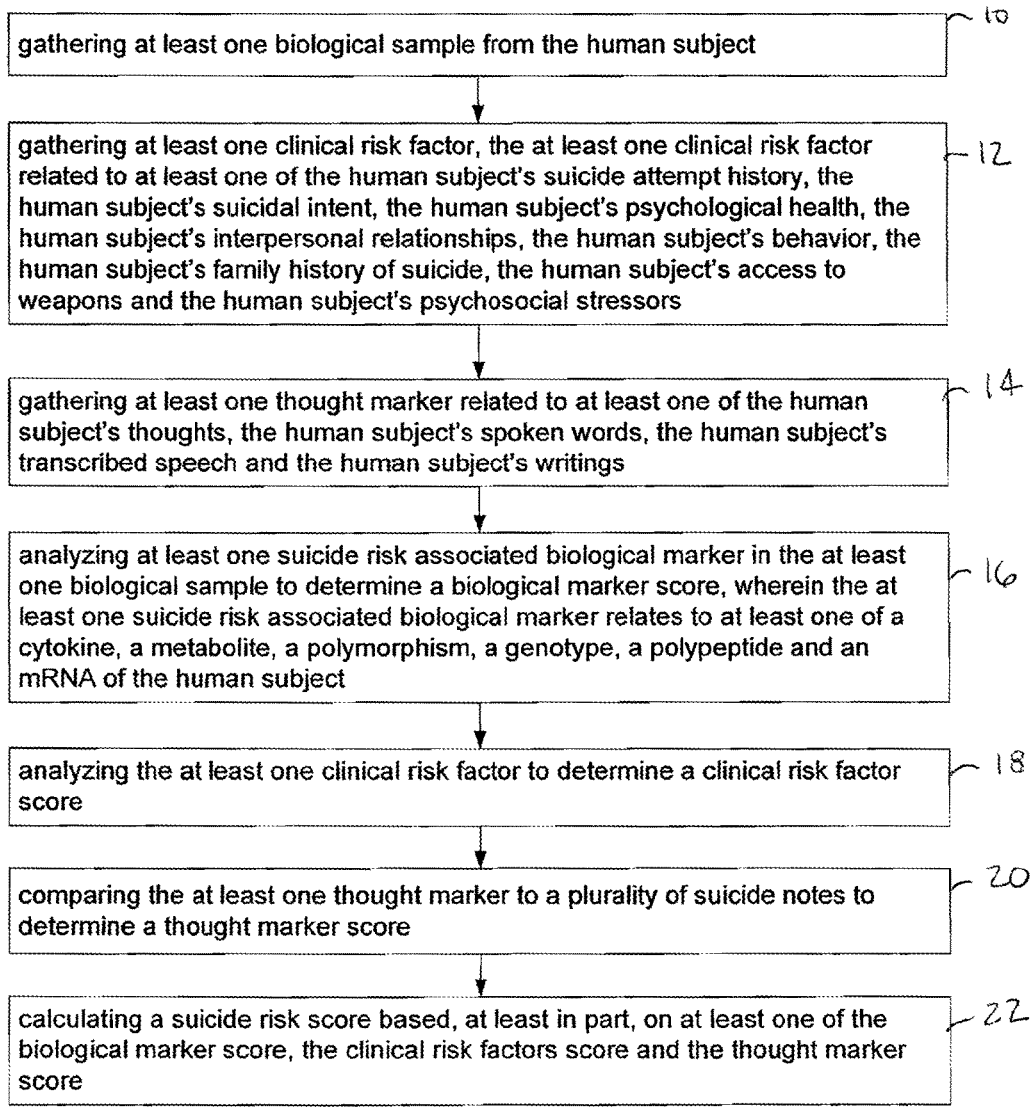
FIG. 1 is a flow diagram depicting an exemplary embodiment of the present invention.

In the following detailed description, reference is made to the accompanying drawings, which form a part hereof. In the drawings, similar symbols typically identify similar components, unless context dictates otherwise. The illustrative embodiments described in the detailed description, drawings, and potential points of novelty are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

This disclosure is drawn to methods and systems related to assessing neuropsychiatric conditions of human subjects. A first example implementation involves assessing suicide risks of human subjects. This first example implementation will be described in detail; and, as will be appreciated by those of ordinary skill, other example implementations described and/or contemplated herein (such as, for example, the end-of-life care assessment and the schizophrenia assessment) will be readily implemented using the methodologies, components and systems of this first example embodiment.

I. Suicide Risk Implementation

As depicted in FIG. 1, this embodiment may include an operation 10 of gathering biological sample(s) from the human subject. This embodiment also may include an operation 12 of gathering clinical risk factor(s) such as the human subject's suicide attempt history, suicidal intent, psychological health, interpersonal relationships, behavior, family history of suicide, access to weapons, psychosocial stressors and/or other similar clinical risk factors. This embodiment further may include an operation 14 of gathering thought marker(s) related to the human subject's thoughts, spoken words, transcribed speech, writings and/or other similar thought markers. This embodiment may further include an operation 16 of analyzing the biological sample to identify suicide risk associated biological marker(s). These suicide risk associated biological marker(s) may relate to cytokine(s), metabolite(s), polymorphism(s), genotype(s), polypeptide(s), mRNA of the human subject and/or other similar biological marker(s).

This exemplary embodiment may include analyzing the biological marker(s) by using known analysis methods including, without limitation, those discussed below. This analysis may result in the determination of a biological marker score. This embodiment may also include a computer-implemented operation 18 of analyzing the clinical risk factor(s) by using known analysis methods including, without limitation, those discussed below. This analysis may result in the determination of a clinical risk factor score. This embodiment may further include a computer-implemented operation 20 of comparing the thought marker(s) to suicide notes (such as those developed from a predetermined suicide note database, for example). This comparison may result in the determination of a thought marker score. This embodiment may further include the computer-implemented operation 22 of calculating a suicide risk score based, at least in part, on the biological marker score(s), the clinical risk factors score(s) and/or the thought marker score(s). The calculation of the suicide risk score may be implemented in many ways, including utilizing averages, weighted formulas, normalization of scores, regressions and/or other similar calculation implementations. This suicide risk score may be provided to the doctor(s), clinician(s), nurse(s), parent(s) or others and may be used in the determination of whether further treatment, counseling, observation or intervention is appropriate (e.g., to help prevent a next or even initial suicide attempt by the patient if the suicide risk score is at or above a certain level).

In another exemplary embodiment, the method may include analyzing biological marker(s) to determine a composite biological marker score. The composite biological marker score may be a score including two or more biological marker scores, each related to a suicide risk associated biological marker. For example, a composite score could be determined based on a cytokine biological marker score, a polymorphism biological marker score and a genotype biological marker score. In that example, the composite biological marker score may be determined by a computerized system in many ways, including utilizing averages, weighted formulas, normalization of scores, regressions and/or other similar calculation implementations. In yet another embodiment, the composite biological marker score may be a score including two or more biological marker scores, each biological marker scores related to the same type of suicide risk associated biological marker. For example, a composite score could be determined based on a first metabolite biological marker score and a second metabolite biological marker score.

Figure 2:
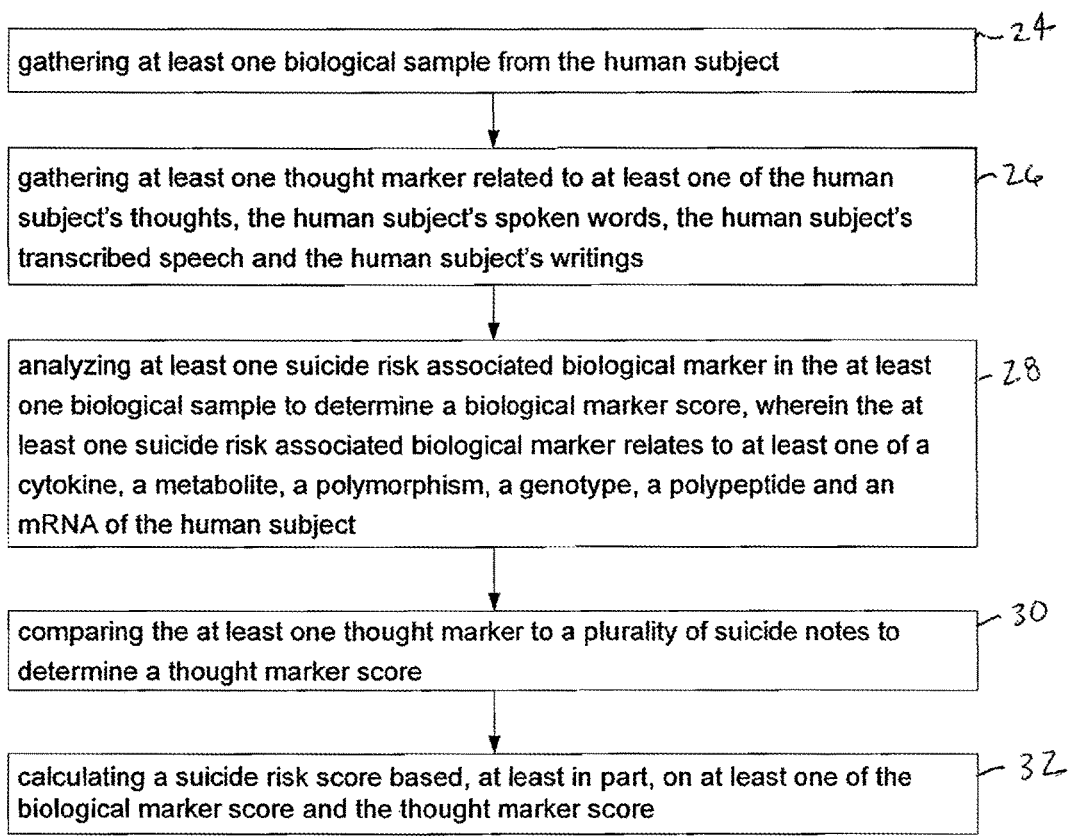
FIG. 2 is a flow diagram depicting another exemplary embodiment of the present invention.

Another exemplary embodiment, as depicted in FIG. 2, may include a method of assessing a suicide risk (initial risk or follow-up risk) of a human subject. This embodiment may include an operation 24 of gathering biological sample(s) from the human subject. This embodiment further may include the operation 26 of gathering thought marker(s) related to the human subject's thoughts, spoken words, transcribed speech, writings and/or other similar thought markers. In this embodiment, the biological sample may include suicide risk associated biological marker(s). These suicide risk associated biological marker(s) may relate to cytokine(s), metabolite(s), polymorphism(s), genotype(s), polypeptide(s), mRNA of the human subject and/or other similar biological marker(s).

This exemplary embodiment may include an operation 28 of analyzing the biological marker(s) by using known analysis methods including, without limitation, those discussed below. This analysis may result in the determination of a biological marker score. This embodiment may further include a computer-implemented operation 30 of comparing the thought marker(s) to suicide notes (such as those developed from a predetermined suicide note database, or a corpus of suicide note language, for example). This comparison may result in the determination of a thought marker score. This embodiment may further include a computer-implemented operation 32 of calculating a suicide risk score based, at least in part, on the biological marker score(s) and/or the thought marker score(s). The calculation of the suicide risk score may be implemented in many ways, including utilizing averages, weighted formulas, normalization of scores, regressions and/or other similar calculation implementations.

In one embodiment, the method may include a tool utilized by a physician in evaluating potential treatment regimens for a patient who has exhibited at least one suicidal attribute such as, but not limited to, a suicide attempt.

Figure 3:
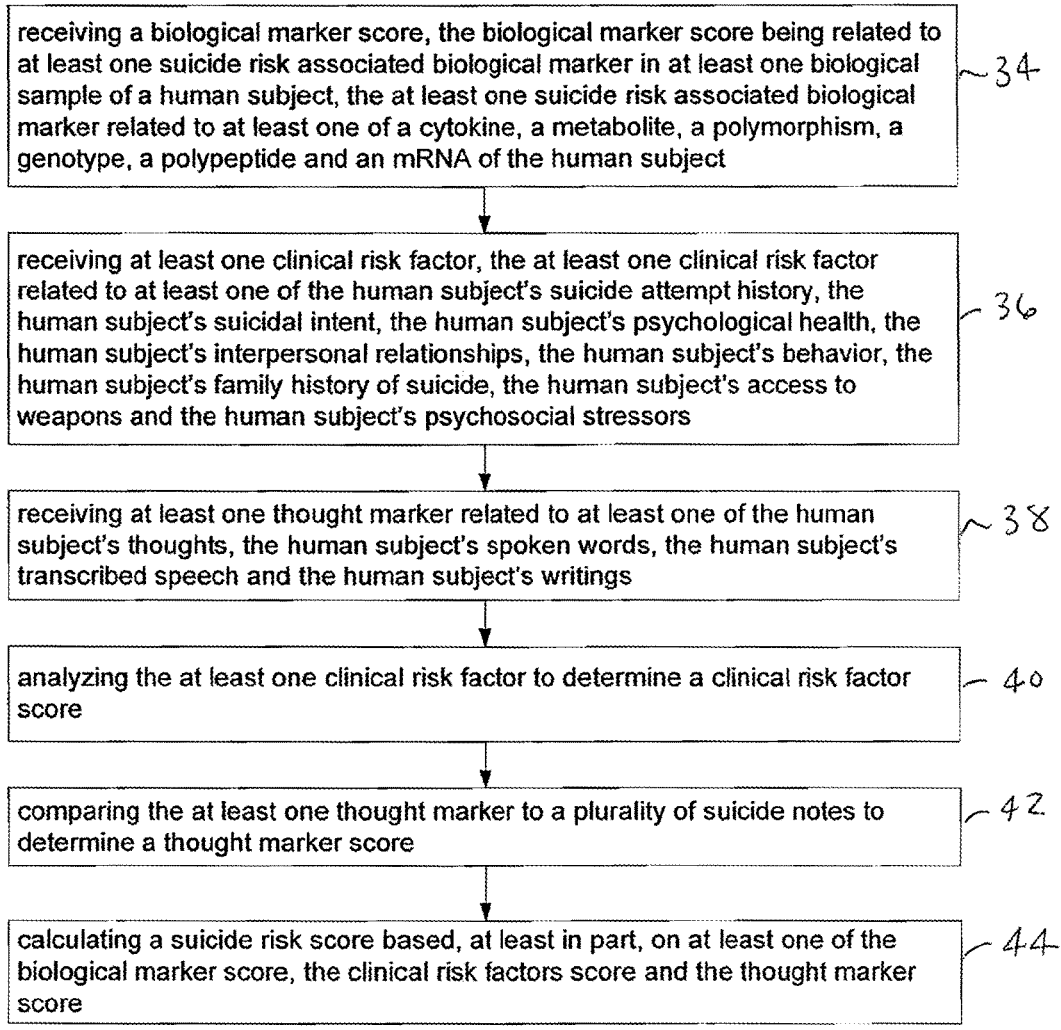
FIG. 3 is a flow diagram depicting another exemplary embodiment of the present invention.

In another exemplary embodiment as depicted in FIG. 3, the invention may include a computer-readable medium having instructions configured to perform computer-implemented operations. These operations may include an operation 34 of receiving biological marker score(s), an operation 36 of receiving clinical risk factor(s) and an operation 38 of receiving thought marker(s). The biological marker score(s) may be related to suicide risk associated biological marker(s) in biological sample(s) of a human subject. The suicide risk associated biological marker(s) may be related to cytokine(s), metabolite(s), polymorphism(s), genotype(s), polypeptide(s), mRNA of the human subject and/or other similar biological marker(s). The clinical risk factor(s) may be related to the human subject's suicide attempt history, suicidal intent, psychological health, interpersonal relationships, behavior, family history of suicide, access to weapons, psychosocial stressors and/or other similar clinical risk factors. The thought marker(s) may be related to the human subject's thoughts, spoken words, transcribed, writings and/or other similar thought markers.

The computer readable instructions in this embodiment may also include instructions for performing the operation 40 of analyzing the clinical risk factor(s) by using known analysis methods including, without limitation, those discussed below. This analysis may result in the determination of a clinical risk factor score. The computer readable instructions in this embodiment may further include instructions for performing the operation 42 of comparing the thought marker(s) to suicide notes (such as those found in a predetermined suicide note database, for example). This comparison may result in the determination of a thought marker score. The computer readable instructions in this embodiment may further include instructions for performing the operation of calculating a suicide risk score based, at least in part, on the biological marker score(s), the clinical risk factors score(s) and/or the thought marker score(s). The calculation of the suicide risk score may be implemented in many ways, including utilizing averages, weighted formulas, normalization of scores, regressions and/or other similar calculation implementations.

Figure 4:
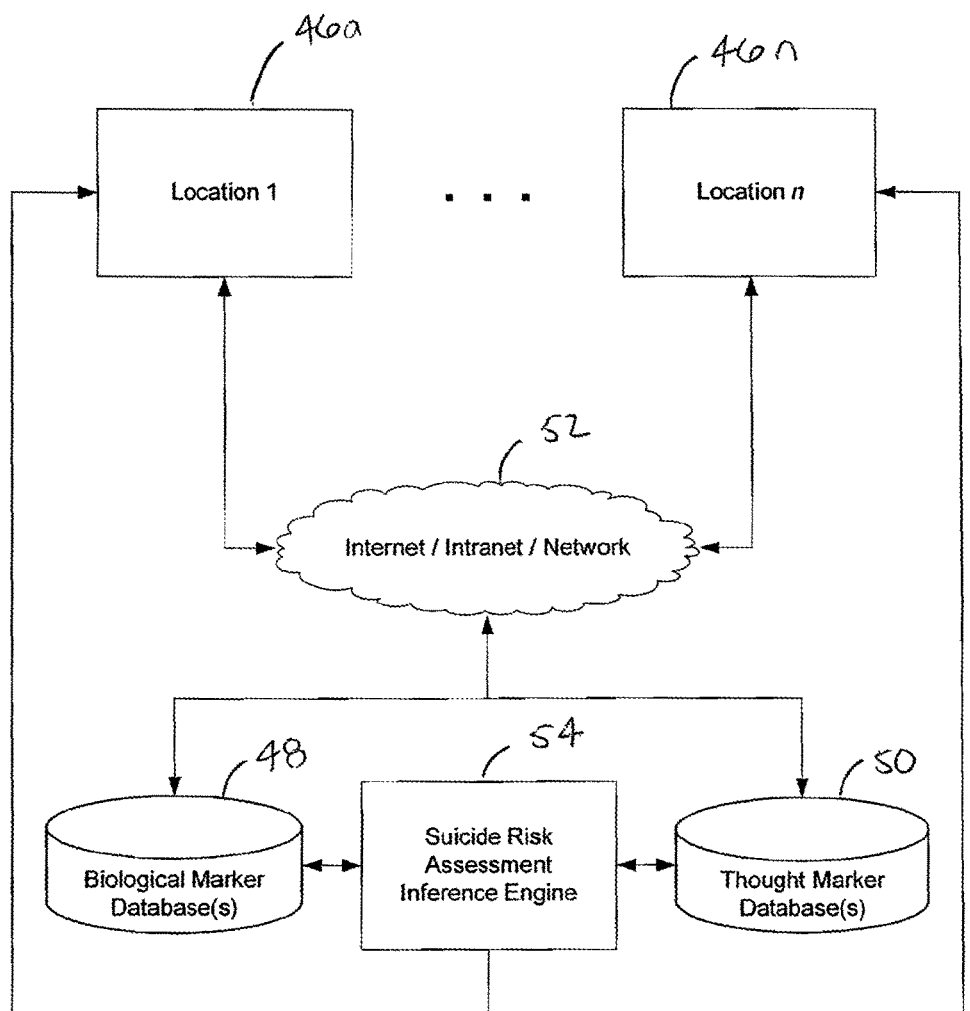
FIG. 4 is a diagram depicting yet another exemplary embodiment of the present invention.

FIG. 4 provides an exemplary system for assessing a suicide risk of a human subject. In this embodiment, users at one or more locations (for example, locations 46a through 46n, where n corresponds to any number) may communicate with biological marker database(s) 48 and thought marker database(s) 50. This communication may be implemented through any network connection 52 (such as the Internet or an intranet, for example). Locations may include medical facilities, hospitals, research facilities, laboratories, blood testing centers and other similar locations. Users may transmit or request and receive data to the biological marker database(s) and thought marker database(s). The biological marker database(s) and thought marker database(s) may also be in communication with a suicide risk assessment inference engine 54. The suicide risk assessment inference engine may receive data from the biological marker database(s) 48 and thought marker database(s) 50 and output a suicide risk score based, at least in part on the data and one or more predefined rule sets. The users at the one or more locations may receive the suicide risk score from the suicide risk assessment inference engine 54.

In yet another embodiment, a system for assessing a suicide risk of a human subject may be provided. This system may include a computer system, server system(s) in communication with the computer system and a suicide risk interface (including a graphical user interface) stored on the server system(s) and accessible by the computer system. The suicide risk interface may provide suicide risk information related to suicide risk associated biological marker(s), clinical risk factor(s) and thought marker(s). In one embodiment, the system may generate a suicide risk score based, at least in part, on the suicide risk associated biological marker(s), the clinical risk factor(s) and/or the thought marker(s). In one embodiment, the suicide risk score may be a numerical value. In another embodiment, the numerical value may be a numerical value that is relative to the numerical value of other human subjects.

In another embodiment, the suicide risk interface may generate a suicide risk quartile based, at least in part, on suicide risk associated biological marker(s), clinical risk factor(s) and thought marker(s), where the suicide risk quartile may be a quartile that is relative to the quartile of other human subjects.

In yet another embodiment, the suicide risk interface may generate a biological marker score based, at least in part, on suicide risk associated biological marker(s), a clinical risk factor score based, at least in part, on the clinical risk factor(s), and a thought marker score based, at least in part, on thought marker(s).

In another embodiment, the suicide risk interface may normalize the biological marker score(s), the clinical risk factor score(s) and/or the thought marker score(s). This normalization may generate normalized biological marker score(s), normalized clinical risk factor score(s) and/or normalized thought marker score(s). In this embodiment, the suicide risk interface may generate a suicide risk score based, at least in part, on the biological marker score(s), the clinical risk factor score(s), the thought marker score(s), the normalized biological marker score(s), the normalized clinical risk factor score(s) and the normalized thought marker score(s).

I.A Biological Analysis

An exemplary embodiment of the present disclosure may provide systems and methods of assessing a suicide risk in a human subject involving gathering at least one biological sample and analyzing at least one suicide risk associated biological marker in the sample to determine a biological marker score.

A "biological sample" may include a sample collected from a subject including, but not limited to, tissues, cells, mucosa, fluid, scrapings, hairs, cell lysates, blood, plasma, serum, and secretions. Biological samples such as blood samples may be obtained by any method known to one skilled in the art.

A "biological marker" may include any physiological indicator such as, but not limited to, the genotype of the subject at a particular loci such as a gene, SNP, or portion of a gene, polymorphism, mRNA, cytokine, metabolite, peptide, polypeptide, hormone, neurotransmitter, or cell type. Any means of evaluating a biological marker known in the art may be utilized in the current methods. A "suicide risk associated" biological marker may include a physiological indicator that has been linked to an abnormal frequency of suicide attempts or suicide completion. Such an abnormal risk may include an elevated frequency of suicide attempts or suicide completion as compared to a healthy population or population of subjects at risk for suicide attempts or suicide completion or a decreased frequency of suicide attempts or suicide completion within a population of subjects at risk for suicide attempts or suicide completion. Exemplary populations of subjects at risk for suicide attempts or suicide completion may include, but are not limited to, subjects who have already made at least one suicide attempt or who have been diagnosed with a disease or condition affiliated with an elevated frequency of suicide attempts or suicide completion, such as schizophrenia.

Suicide risk associated genotypes may include, but are not limited to, suicide risk associated SNPs and allelic variations larger than a single nucleotide within the coding region of a gene, the exon-intron boundaries, or the 5' upstream regulatory region of a gene linked to an abnormal frequency of suicide attempts or completions. It is contemplated that suicide risk associated genotypes may include, but are not limited to, the S and L alleles of the 5' upstream regulatory region of the serotonin transporter gene (5-HTTLPR) (Weizman, 2000 "Serotonin transporter polymorphism and response to SSRIs in major depression and relevance to anxiety disorders and substance abuse", *Pharmacogenomics*, 1:335-341; herein incorporated by reference in its entirety).

A suicide risk associated SNP may include, but is not limited to, a single nucleotide polymorphism (SNP) for which at least one variant has been linked to an abnormal frequency of suicide attempts or completions. It is contemplated that suicide risk associated SNP's may include, but are not limited to, A218C and A779C of the TPH1 gene and A59G of the SLC6A3 gene (Bondy et al (2006) "Genetics of Suicide", *Molecular Psychiatry*, 11(4) 336-351 and U.S. 2007/0065821, herein incorporated by reference in their entirety).

Suicide risk associated mRNAs may include, but are not limited to, altered mRNA levels of a gene linked to an abnormal frequency of suicide attempts or completions. It is contemplated that suicide risk associated mRNAs may include, but are not limited to, the 5-HT(2A) mRNA in the prefrontal cortex and hippocampus (Pandey (2002) "Higher Expression of serotonin 5-HT(2A) receptors in the postmortem brains of teenage suicide victims" *American J. Psychiatry* 159:419-429, herein incorporated by reference in it's entirety). Suicide risk associated polypeptides may be polypeptides linked to an abnormal frequency of suicide attempts or completions.

Suicide risk associated cytokines may include, but are not limited to, cytokines linked to an abnormal frequency of suicide attempts or completions. It is contemplated that suicide risk associated cytokines may include, but are not limited to, IL-6, IL-2, IFN-γ, IL-4 and TGF-β1. See for example Shaffer et al (1996) "Psychiatric diagnosis in child and adolescent suicide", *Arch Gen Psychiatry* 53:339-348 and Kim et al (2007) "Differences in cytokines between non-suicidal patients and suicidal patients in major depression", *Prog Neuropsychopharmacol Biol Psychiatry*, 32:356-61, herein incorporated by reference in their entirety). Increased IL-6 production may be correlated with decreased risk of suicide attempt or completion. Decreased IL-2 may be correlated with increased risk of suicide attempt or completion. A shift in the ratio of Th1 and Th2 cell types toward the Th1 cell types may be associated with decreased risk of suicide attempt or completion.

Suicide risk associated neurotransmitters may include, but are not limited to, neurotransmitters linked to an abnormal frequency of suicide attempts or completions. It is contemplated that suicide risk associated neurotransmitters may include, but are not limited to, serotonin (5-HT). See for example Pandey (1997) "Protein kinase C in the post mortem brain of teenage suicide victims", *Neurosci Lett* 228:111-114 and Samuelsson (2006) "CSF 5-H1AA, suicide intent and hopelessness in the prediction of early suicide in male high risk suicide attempters" *Acta Psychiatr Scanda* 113:44-47, herein incorporated by reference in their entirety.

Suicide risk associated metabolites may include, but are not limited to, metabolites either directly linked to an abnormal frequency of suicide attempts or completions or a metabolite of a biological compound linked to an abnormal frequency of suicide attempts or completions. It is contemplated that suicide risk associated metabolites may include, but are not limited to, 5-hydroxyindoleacetic acid (5HIAA), a metabolite of serotonin. Low 5HIAA levels may be linked to elevated risk of suicide attempt or suicide completion. See Nordstrom (1994) "CSF 5-HIAA predicts suicide risk after attempted suicide", *Suicide Life Threat Behav* 24:1-9, herein incorporated by reference in its entirety. The number of different metabolites in humans is unknown but range from approximately 2000 to approximately 20,000 compared with significantly higher numbers of proteins and genes (Claudino et al (2007) "Metabolomics: available results, current research projects in breast cancer, and future applications", *J. Clinical Oncology* 25:2840-2846, herein incorporated by reference in its entirety. These small molecule metabolites may be found in biological samples such as serum or urine. Mass spectroscopy may be used to analyze an individual metabolite or collection of metabolites. See, for example, Wu et al, (2008), "High-throughput tissue extraction protocol for NMR and MS-based metabolomics", *Analytical Biochemistry* 372:204-212 and Yee et al (2002) "An NMR Approach to Structural Proteomics", PNAS 99:1825-30, herein incorporated by reference in their entirety.

Any method of analyzing a biological marker known in the art may be utilized in the present methods. Methods of analyzing suicide risk associated biological markers may include, but are not limited to, RT-PCR array profiling such as the Human Th1-Th2-Th3 PCR Array (SABiosciences), DNA microarrays, immunogenic methods, mass spectroscopy, HPLC, NMR, DNA sequencing, genotyping, PCR, reverse transcription-PCR, real-time PCR, MALDI-TOF, HPLC, gas chromatography mass spectrometry (GC-MS), liquid chromatography mass spectrometry (LC-MS), Fourier transform mass spectrometry (FT-MS), electron paramagnetic resonance (EPR) spectrometry, atomic force microscopy, and Raman spectroscopy, solid phase ELISA, fluid phase multi-analyte analysis, fluorescent bead based immunoassay, sandwich based immunoassays, and expression analysis (see for example Domon et al (2006) "Mass Spectrometry and Protein Analysis, Science 312:212-217; Walker (2003) *Protein Protocols Handbook*, 2$^{nd}$ ed, Humana Press; and Walker (2005) *Proteomics Protocols Handbook*, Humana Press; Winning et al (2007) "Quantitative Analysis of NMR Spectra with Chemometrics", *Journal of Magnetic Resonance* 190:26-32; Bowtell & Sambrook (2003) *DNA Microarrays* Cold Spring Harbor Laboratory Press; herein incorporated by reference in their entirety.)

Different methods of analyzing suicide risk associated biological markers may generate different data types. For instance, mass spectroscopy may generate a mass/charge ratio while SNP genotyping may indicate the presence or absence of a particular nucleotide at a specified residue. Analysis of other biological markers may yield data about the concentration of the biomarker, relative concentration data (such as in gene expression analysis), or a detectable v. non-detectable indication. The raw data obtained for each biomarker may be normalized before information about a particular biomarker is incorporated in the biological marker score.

The following examples are offered by way of illustration and not limitation.

EXPERIMENTAL

EXAMPLE 1. Biological Sample Collection

Whole blood samples are collected from a human subject using clinically acceptable blood collection methods. Two aliquots of 8.5 ml whole blood are drawn from the subject. One aliquot is centrifuged to separate cells and sera. Serum samples (200 µl) are utilized in NMR and mass spectrometry analysis or cytokine analysis. An additional sample in a purple-top (EDTA containing) tube is utilized in molecular genetic analysis. (Additional blood samples are obtained and analyzed if the patient becomes suicidal after the initial evaluation.)

EXAMPLE 2. Blood Sample Preparation for NMR Studies

Blood samples for Nuclear Magnetic Resonance (NMR) studies are thawed. 400 µl saline (0.9% NaCl in 10% $D_2O$ (deuterium oxide) is mixed with the blood sample. The samples are centrifuged at 13400 g for 5 minutes prior to NMR analysis. The blood is prepared according to NMR and clinical standards.

EXAMPLE 3. NMR Data Collection and Analysis

NMR data is collected using a Bruker US2 Avance II NMR spectrometer (Bruker Biospin, Rheinstettin, Germany) operating at 850 MHz $^1$H frequency and 298K. Data is zero-filled by a factor of two and exponentially weighted by 0.3 Hz of line broadening prior to Fourier transform, followed by spectral phasing and baseline correction.

Processed spectra are prepared for principal component analysis (PCA) using AMIX. When distinct clustering patterns are observed, models are built for each class. Robust models are selected from these models and are investigated to identify spectral outlier regions correlated with suicide risk. When significant loadings are identified, chemical analysis methods are combined with the spectral analysis.

EXAMPLE 4. HPLC and HPLC Analysis

Liquid chromatography in the LC-MS system is conducted using an Agilent Technologies 1200 series HPLC. The LC-MS instrument collects raw data in the form of individual mass spectra at each time point in the total ion chromatogram. Individual LC-MS analyses are loaded into the sample table in the Bruker Profile Analysis software package (Bruker Daltonics).

EXAMPLE 5. DNA Analysis

The Promega Magnesil RED silica-coated magnetic bead kit on a KingFisher 96 robotic magnetic bead manipulator is used to extract DNA from a blood sample.

I.B. Clinical Analysis

An embodiment of the present disclosure may provide systems and methods of assessing a suicide risk in a human subject involving gathering clinical risk factor(s) and analyzing the clinical risk factor(s) to determine a clinical risk factor score.

Clinical characteristics about a human subject may be collected during patient interviews, from medical record databases and/or other similar means. Medical and/or mental health staff may administer interviews with a subject and/or the subject's parent(s) or guardian(s).

Clinical factors that increase the risk of completed suicide in children and adolescents may include (without limitation): high suicidal intent as evidenced by planning, timing and method, a history of previous suicide attempts, a high level of interpersonal discord, a presence of a mood disorder, substance use, a history of impulsive aggression, a family history of suicidal behavior, access to weapons such as firearms, and recent psychosocial stressors such as conflicts with authority, breakups with significant others or legal issues. Other clinical risk factors may include evidence of planning, timing the attempt to avoid detection, not confiding suicidal plans ahead of time and expressing a wish to die.

In one or more embodiments, a prior suicide attempt may be a primary risk factor for youth suicide, and may greatly elevate the risk of a subsequent suicide completion. The risk for another attempt may be high in the first 3 to 6 months after an unsuccessful suicide attempt, and the risk may remain elevated for at least several years. Suicidal intent may be another indicator and risk factor for repetition of suicide attempts and completed suicide.

In an exemplary embodiment, clinical interviews with a subject and/or their parent(s) or guardian(s) may include oral and/or written interviews. Examples of such interview tools may include (without limitation):
1. Background form(s) to elicit demographics information
2. Suicide history form(s) to elicit exposure to suicide, connectedness to family, history of neglect or abuse, access to firearms, sleep habits, etc.
3. The Columbia suicide history form(s) to elicit information about lifetime suicide attempts.
4. The Suicide Intent Scale (SIS) to evaluate the severity of suicidal intent for a previous suicide attempt.
5. Family History-Research Diagnostic Criteria (FH-RDC) to diagnose psychiatric illnesses in first- and second-degree relatives of subjects.
6. Affective Story Task for Speech Sample to measure "Theory of Mind" ability within the context of emotionally charged situations. This may be a measure of false-belief understanding (e.g. one character's beliefs about the mental state of another character) and consists of positive-, neutral- and negative-valenced stories. Stories may be matched on word length, complexity (e.g. details, dialogue, characters and events) and semantic structure. The positive, neutral and negative stories may include content consistent with subjective experience of respectively manic, euthymic or depressed states. Three stories from each condition may be generated, and each subject may receive one story from each of the three conditions. Each story may be read aloud to the interview subject, and the order of conditions may be counterbalanced across subjects to control for order effects. Stories may be gender specific; female subjects may receive a female story version and male subjects may receive a male story version. Subjects may be assessed on their ability to recognize that a misleading series of events could lead one of the characters in the story to develop a false belief about another character's mental state. At the end of each story, the subject may be asked a false-belief question that assesses whether the subject recognized the potential for misunderstanding. Subject responses may be recorded and transcribed into a secure database. The choice of transcribed speech is pragmatic. That is, in an emergency situation it may be unreasonable to ask the suicidal patient to write. It may be, however, practical to ask questions of those patients who are conscious and to receive answers. These interviews may be retained for subsequent analysis.

In an exemplary embodiment, clinical interviews with just the subject may include oral and/or written interviews. Examples of such interview tools may include (without limitation):

1. Suicide Probability Scale (SPS): a tool for rating "normals," a psychiatric inpatient group, and a suicide attempter group.
2. Youth Risk Behavior Survey: a tool related to personal safety, suicide attempt, tobacco use, alcohol and drug use, sexual activity, etc.
3. Stressful Life Events Schedule (SLES): a tool yielding information on the occurrence, the date of occurrence, the duration, and the perceived threat of events experienced by the patient.
4. Achenbach Youth Self-Report/11-18 (YSR): A tool for 5th grade reading skills that obtains reports from parents, relatives and/or guardians about children's competencies and behavioral/emotional problems.
5. Affective Story Task for Speech Sample (as discussed previously).

In an exemplary embodiment, clinical interviews with just the parent(s) and/or guardian(s) may include oral and/or written interviews. Examples of such interview tools may include (without limitation):

1. Achenbach Child Behavior Checklist for Ages 6-18 (CBCL/6-18).
2. Stressful Life Events Schedule (SLES) (as described previously)
3. Conflict behavior questionnaire form(s)

I.C. Thought Analysis

An embodiment of the present disclosure may provide methods of assessing a suicide risk in a human subject involving gathering thought marker(s) and comparing the thought marker(s) to a plurality of suicide notes to determine a thought marker score. Natural language processing methods may be conducted to determine a correlation between the thought marker(s) and a suicide notes database. U.S. patent application Ser. No. 12/006,813, entitled, *Processing Text with Domain-Specific Spreading Activation Methods*, by Pestian et. al., provides examples of certain natural language processing methods that may be used with present embodiments.

Suicide notes may essentially be artifacts of suicidal thought. It is contemplated that machine-learning methods can successfully differentiate a suicide note (or suicide note wording) from a non-suicide writing (or non-suicide note wording). Such machine-learning methods may be implemented as software instructions. Such machine-learning methods may include linguistic analysis (including open source algorithms available in "Perl" language, for example). This linguistic analysis may include spell checking, tokenizing, filtering, stemming, outlier removal and normalization. Testing of exemplary machine-learning methods proved to be about 78% accurate at identifying a suicide note.

Additional analyses may include: mean number of words per sentence, proportion of ambiguous words, percent similarity (the proportion of words that were shared between two different corpora—a suicide note database and WordNet, an English language lexical database, for example), relative entropy (amount of information contained in one corpus [suicidal patients, for example] compared to another corpus [control patients]), and Squared Chi-square distance. Other known analyses may also be implemented.

A number of machine-learning methods may be applied to the transcribed data to test for differences between suicide notes and non-suicide note writings. One tool for this analysis may be the Waikato Environment for Knowledge Analysis (Weka). Specificity, sensitivity and F1 may be computed. Methods useful in this research may be organized into five categories.

Decision trees may include: J48/C4.5, Logistic Model Trees, DecisionStump and M5P.

Classification Rules may include: JRIP, Repeated Incremental Pruning to Produce Error Reduction (RIPPER), M5Rules, OneR, and PART.

Function models may include: Sequential minimal optimization, PolyKernel, Puk, RBFKernel, Logistic, and Linear Regression.

Lazy Learners or Instance-based learner methods may include: IBk and LBR.

Meta learner methods may include: AdaBoostM1, Bagging, LogitBoost, MultiBoostAB and Stacking.

Exemplary thought analysis and machine learning methods may include one or more of the following components: feature selection, expert classification, word mending, annotation and machine learning.

Feature Selection. Feature selection, also called variable selection is a data reduction technique for selecting the most relevant features for a learning models. As irrelevant and redundant features are removed the model's accuracy increases. Multiple methods for feature selection may be used: bag-of-words, latent semantic analysis and heterogeneous selection. In one example, heterogeneous selection may be used. To reduce co-linearity, highly correlated features may be removed; to increase the certainty that a feature is not randomly selected, that feature may be required to appear in at least 10% of the documents.

Parts of Speech. A first step may be to tokenize each sentence to determine if additional analysis is feasible. This may be done, for example, using a custom Perl program. Next, using the Penn-Treebak tag set and/or using The Lingua-EN-Tagger-0.13, 2004 module, for example, several part of speech tags may be added to the feature space. This tagging may be beneficial to establish the relationship of a particular word to a particular concept.

Readability. The Flesch and Kincaid readability scores may produce a high information gain and may be included in the feature space. These scores are designed to indicate comprehension difficulty. They include an ease of reading and text-grade level calculation. Computation of the Flesch and Kincaid indexes may be completed by adding the Lingua::EN::Fathom module to the exemplary Perl program.

Suicidal Emotions. Collected suicide notes may be annotated with emotional concepts. Developing an ontology to organize these concepts may utilize both the Pubmed queries and expert literature reviews. Using the Pubmed queries, a frequency analysis of the key-words in a collection (e.g. 2,000) of suicide related manuscripts may be conducted. Expert review of those keywords may yield a subset of suicide related manuscripts that contain suicide emotional concepts. These emotional concepts may be allocated to a plurality of different classes. Several mental health professional may then review each of the collected suicide notes, and assign the emotional concepts found in those notes to the appropriate classes. For example, the emotional concepts of guilt may be assigned to the class of emotional states.

Machine Learning. There are multiple general types of machine learning: unsupervised, semi-supervised and supervised. Semi-supervised methods use both labeled and unlabeled data and is efficient when labeling data is expensive, which leads to small data sets. In an example approach, the semi-supervised approach may be selected mainly because the labeled data may be small. Additionally, exemplary machine learning algorithms for that may be used, without limitation, may be organized into five categories: Decision trees: J48/C4.5, Logistic Model Trees, Decision Stump and M5P; Classification Rules: JRIP, Repeated incremental Pruning to Produce Error Reduction (RIPPER), M5Rules, OneR, and PART; Function models: Sequential minimal optimization (SMO, a variant of SVM), PolyKernel, Puk, RBF Kernel, Logistic, and Linear Regression; Lazy Learners or Instance-based learner: Ibo and LBR; Meta learners; AdaBoostM1, Bagging, Logit Boost, Multi Boost AB and Stacking.

Machine categorization. The following algorithms may be used to extract and quantify relevant content features and create a heterogeneous, multidimensional feature space:

1. Structure: number of paragraphs,
2. Spelling: number of misspellings (perl module Text::SpellChecker).
3. Tagging: number of tokens, number of words, number of non-word characters, number of sentences, mean frequency of a word, standard deviation of frequency of a word, maximal frequency of a word, mean length of a sentence, standard deviation of length of a sentence, maximal length of a sentence, frequency of 32 parts of speech (perl module Lingua::EN::Tagger).
4. Readability: Flesch-Kincaid grade level, Flesch reading ease (perl module Lingua::EN::Fathom).
5. Parsing: mean depth of a sentence, standard deviation of depth of a sentence, maximal depth of a sentence (perl module Lingua::CollinsParser.

Features arrived from different sources; and so, their numeric values naturally fall in different ranges. For certain machine categorization algorithms that means that some features would become more important than others. To remedy this problem, feature values were normalized based on a maximum value of one. this created a matrix with 66 documents and 49 features and values between 0 and 1. Since there are fewer features than documents, features selection was not applied.

Algorithm Classification

Decision trees. Classifier may be represented as a tree. Every node of a tree may be represented by a decision list. The decision about which branch to go to next may be based on a single feature response. Leaves of the tree may be represented by the decisions about which class should be assigned to a single document. The following algorithms may be used:

J48 generates un-pruned or pruned C4.5 revision for 8 decision trees.

LMTimplements 'Logistic Model Trees.

Decision Stump implements decision stumps (trees with a single split only, i.e. one-level-decision trees), which are frequently used as base learners for meta learners such as Boosting.

Classification rules. Classifier may be represented by a set of logical implications. If a condition for a document is true, then a class is assigned. Condition may be composed of a set of feature responses OR-ed or AND-ed together. These rules can also be viewed as a simplified representation of a decision tree. The following algorithms may be used:

JR implements a fast propositional rules learner, "Repeated Incremental Pruning to Produce Error Reduction" (RIPPER).

OneR builds a simple 1R classifier; it is a set of rules that test a response of only one attribute.

PART generates a set of simplified rules from a C4.5 decision tree.

Function models. Classifiers can be written down as mathematical equations. Decision trees and rules typically cannot. There are 2 example classifiers in this category. The following algorithms may be used:

SMOI implements a sequential minimal optimization algorithm for training a support vector classifier using linear kernel.

Logistic builds multinomial logistic regression models based on ridge estimation.

Lazy learners. Classifiers in this category may not work until classification time.

Instance-based learning. May be done by reviewing every instance in the training set separately. An example algorithm that may be used in this category:

Ibo' provides a k-nearest neighbors classifier, which uses Euclidean metric as a distance measure.

Bayesian classifiers. Classifiers use Bays theorem and the assumption of independence of features. An example algorithm that may be used in this category:

NB implements the probabilistic Naive Bayes classifier.

I.D. Suicide Risk Score Analysis

An embodiment of the present disclosure may provide methods of assessing a suicide risk in a human subject involving calculating a suicide risk score based, at least in part, on biological marker score(s), clinical risk factors score(s) and thought marker score(s). Such calculation may be implemented in a variety of implementations. In one embodiment, a single suicide risk score may be calculated. Such a score may assist physicians and/or medical employee in determining how likely a subject is to attempt suicide upon or after being released from a medical facility.

In an example embodiment, factors of the suicide risk score calculations may include biological marker(s), clinical risk factor(s) and thought marker(s). The example table below identifies factors, measurement tool(s), method(s) and example result ranges for each factor.

| Factor | Measurement tool(s) | Method(s) | Example Result Range |
| --- | --- | --- | --- |
| Biological Marker(s) | Mass-spectrometry of 5-HIAA, cytokines, genomic analysis | Mass/charge ratio | 3.0-13.0 |

-continued

| Factor | Measurement tool(s) | Method(s) | Example Result Range |
|---|---|---|---|
| Thought Marker(s) | Comparison of subject's thoughts to suicide note database | Machine-learning methods and correlation. | 0.0-1.0 |
| Clinical Risk Factor(s) | Subject and parent/guardian interviews | Percentage of risks present in patients as compared to all risks. | 0.0-1.0 |

Analyses may include independent factor analysis of biological marker(s), clinical risk factor(s) and thought marker(s), as discussed previously.

Data for one or more factors may be normalized between zero and one to create a composite score of the biological marker(s), clinical risk factor(s) and thought marker(s) and their interaction.

In one embodiment (as shown in the table above), biological markers may be reported as a scale from 3-13, where a lower concentration may be of more concern. On the other hand, regarding the clinical risk factor(s) and thought marker(s), a higher concentration may be of more concern. In this case, the biological marker(s) may be normalized using $1-(Patient_i-min(Range_i)/max(Range_i)-min(Range_i))$. In this case, the clinical risk factor(s) and thought marker(s) may be normalized using $-(P_i-min(Range_i)/max(Range_i)-min(Range_i))$. An example of such normalizations is shown in the table below. In this table, a suicide risk score two patients is calculated as a mean of the biological marker score, clinical risk factor score and thought marker score.

In another embodiment, the subject's quartile rank as compared to a database of other subjects may be calculated. Quartiles (as shown in the table below) may provide some decision support without purporting exactness.

|  | Biological Marker Score | Thought Marker Score | Clinical Risk Factor Score | Suicide Risk Score (SRS) | SRS x 10 for ease of reading | Quartile Position |
|---|---|---|---|---|---|---|
| Patient 1 | 3 | 0.78 | 0.6 |  |  |  |
| Normalized | 1.00 | 0.78 | 0.6 | 0.79 | 8 | 1st |
| Patient 2 | 9 | 0.45 | 0.6 |  |  |  |
| Normalized | 0.40 | 0.45 | 0.6 | 0.48 | 5 | 3rd |

To provide additional context for various aspects of the present invention, the following discussion is intended to provide a brief, general description of a suitable computing environment in which the various aspects of the invention may be implemented. One exemplary computing environment is depicted in FIG. 4. While one embodiment of the invention relates to the general context of computer-executable instructions that may run on one or more computers, those skilled in the art will recognize that the invention also may be implemented in combination with other program modules and/or as a combination of hardware and software.

Generally, program modules include routines, programs, components, data structures, etc., that perform particular tasks or implement particular abstract data types. Moreover, those skilled in the art will appreciate that aspects of the inventive methods may be practiced with other computer system configurations, including single-processor or multi-processor computer systems, minicomputers, mainframe computers, as well as personal computers, hand-held wireless computing devices, microprocessor-based or programmable consumer electronics, and the like, each of which can be operatively coupled to one or more associated devices. Aspects of the invention may also be practiced in distributed computing environments where certain tasks are performed by remote processing devices that are linked through a communications network. In a distributed computing environment, program modules may be located in both local and remote memory storage devices.

A computer may include a variety of computer readable media. Computer readable media may be any available media that can be accessed by the computer and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD ROM, digital video disk (DVD) or other optical disk storage, magnetic cassettes, magnetic tape, magnetic disk storage or other magnetic storage devices, or any other medium which may be used to store the desired information and which may be accessed by the computer.

An exemplary environment for implementing various aspects of the invention may include a computer that includes a processing unit, a system memory and a system bus. The system bus couples system components including, but not limited to, the system memory to the processing unit. The processing unit may be any of various commercially available processors. Dual microprocessors and other multi processor architectures may also be employed as the processing unit.

The system bus may be any of several types of bus structure that may further interconnect to a memory bus (with or without a memory controller), a peripheral bus, and a local bus using any of a variety of commercially available bus architectures. The system memory may include read only memory (ROM) and/or random access memory (RAM). A basic input/output system (BIOS) is stored in a non-volatile memory such as ROM, EPROM, EEPROM, which BIOS contains the basic routines that help to transfer information between elements within the computer, such as during start-up. The RAM may also include a high-speed RAM such as static RAM for caching data.

The computer may further include an internal hard disk drive (HDD) (e.g., EIDE, SATA), which internal hard disk drive may also be configured for external use in a suitable chassis, a magnetic floppy disk drive (FDD), (e.g., to read from or write to a removable diskette) and an optical disk drive, (e.g., reading a CD-ROM disk or, to read from or write to other high capacity optical media such as the DVD). The hard disk drive, magnetic disk drive and optical disk drive may be connected to the system bus by a hard disk drive interface, a magnetic disk drive interface and an optical drive interface, respectively. The interface for external drive implementations includes at least one or both of Universal Serial Bus (USB) and IEEE 1394 interface technologies.

The drives and their associated computer-readable media provide nonvolatile storage of data, data structures, computer-executable instructions, and so forth. For the computer, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules may be stored in the drives and RAM, including an operating system, one or more application programs, other program modules and program data. All or portions of the operating system, applications, modules, and/or data may also be cached in the RAM. It is appreciated that the invention may be implemented with various commercially available operating systems or combinations of operating systems.

A user may enter commands and information into the computer through one or more wired/wireless input devices, for example, a keyboard and a pointing device, such as a mouse. Other input devices may include a microphone, an IR remote control, a joystick, a game pad, a stylus pen, touch screen, or the like. These and other input devices are often connected to the processing unit through an input device interface that is coupled to the system bus, but may be connected by other interfaces, such as a parallel port, an IEEE 1394 serial port, a game port, a USB port, an IR interface, etc.

A display monitor or other type of display device may also be connected to the system bus via an interface, such as a video adapter. In addition to the monitor, a computer may include other peripheral output devices, such as speakers, printers, etc.

The computer may operate in a networked environment using logical connections via wired and/or wireless communications to one or more remote computers. The remote computer(s) may be a workstation, a server computer, a router, a personal computer, a portable computer, a personal digital assistant, a cellular device, a microprocessor-based entertainment appliance, a peer device or other common network node, and may include many or all of the elements described relative to the computer. The logical connections depicted include wired/wireless connectivity to a local area network (LAN) and/or larger networks, for example, a wide area network (WAN). Such LAN and WAN networking environments are commonplace in offices, and companies, and facilitate enterprise-wide computer networks, such as intranets, all of which may connect to a global communications network such as the Internet.

The computer may be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi (such as IEEE 802.11x (a, b, g, n, etc.)) and Bluetooth™ wireless technologies. Thus, the communication may be a predefined structure as with a conventional network or simply an ad hoc communication between at least two devices.

The system may also include one or more server(s). The server(s) may also be hardware and/or software (e.g., threads, processes, computing devices). The servers may house threads to perform transformations by employing aspects of the invention, for example. One possible communication between a client and a server may be in the form of a data packet adapted to be transmitted between two or more computer processes. The data packet may include a cookie and/or associated contextual information, for example. The system may include a communication framework (e.g., a global communication network such as the Internet) that may be employed to facilitate communications between the client(s) and the server(s).

Figure 5:
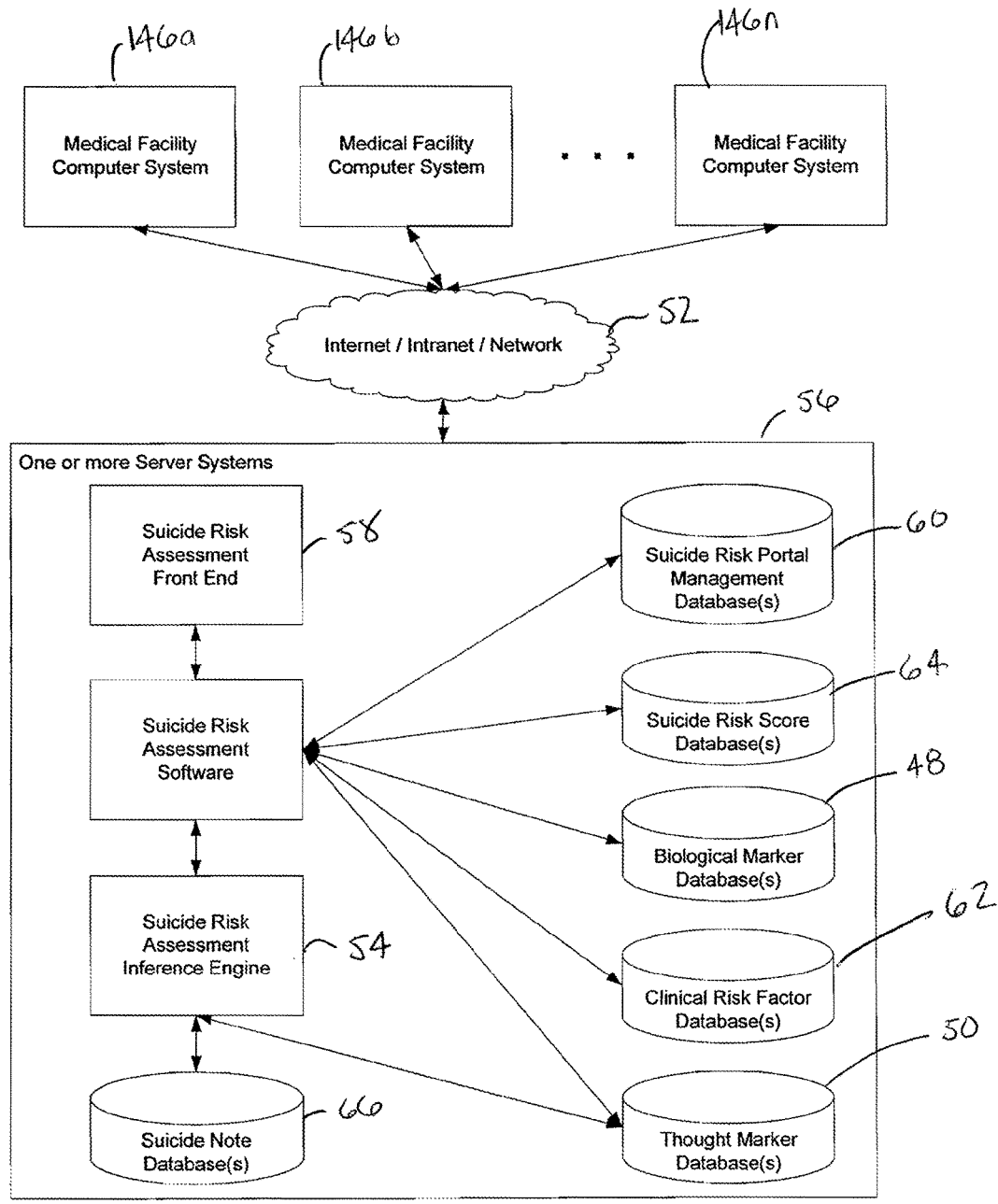
FIG. 5 is a diagram depicting another exemplary embodiment of the present invention.

In one exemplary embodiment, as depicted in FIG. 5, medical facility computer system(s) 146a, 146b . . . 146n, may be in communication with server system(s) 56. This communication may be implemented through any network connection 52 (such as the Internet or an intranet, for example). The server system(s) may include software instructions, database(s), and inference engine and/or a front end (such as a graphical user interface, for example). In the embodiment shown in FIG. 5, the software instructions stored on the server(s) may be configured to implement a suicide risk interface. The server(s) may also be configured to provide a suicide risk assessment front end 58. This front end may be provide to the medical facility computers (146a-n) user interface, a graphical user interface or other similar front end. The server(s) may also store one or more databases that may include management databases 60, biological marker databases 48, clinical risk factor databases 62, thought marker databases 50, suicide risk score databases 64 and/or suicide note language databases 66. The management database(s) 60 may be configured to store and make accessible data used by the suicide risk interface software instructions, among other components. The biological marker database(s) 48 may be configured to store and make accessible data associated with biological markers. The clinical risk factor database(s) 62 may be configured to store and make accessible data associated with clinical risk factors. The thought marker database(s) 50 may be configured to store and make accessible data associated with thought markers. The suicide risk score database(s) 64 may be configured to store and make accessible data associated with biological marker scores, clinical risk factor scores, thought marker scores, suicide risk scores, quartiles and other similar data. The suicide note language database(s) 66 may be configured to store and make accessible data associated with suicide note language, such as providing a corpus of suicide note language.

II. End-Of-Life Assessment and Care Implementation

Beyond the long-standing traditional method of regular conversation with the terminally ill patient, the present example implementation provides that at least two additional sources of information may aide the caregiver in understanding the needs of the dying child and their family. They are thought-markers and biomarkers. Thought-markers can be described as artifacts of thought that are expressed through conversations and writings. First order thought-markers may include writings and transcribed conversations of the individual. Second order thought-markers may include items like facial expressions or the natural pauses during conversation.

A second source of information are biomarkers that potentially change as death approaches. Some biomarkers that are related to tracking death include C-reactive protein (Erlinger, T. P., et al., "C-reactive protein and the risk of incident colorectal cancer," JAMA, 2004. 291(5): pp. 585-90; and Clarke, R., et al., "Biomarkers of inflammation predict both vascular and non-vascular mortality in older men," Eur Heart J, 2008. 29(6): pp. 800-9), NGal (Mishra, J., et al., "Neutrophil gelatinase-associated lipocalin (NGAL) as a biomarker for acute renal injury after cardiac surgery," Lancet, 2005. 365(9466): pp. 1231-8), cystatin C (Gronroos, M. H., et al., "Comparison of glomerular function tests in children with cancer; and Shlipak, M. G., et al., "Cystatin C and the risk of death and cardiovascular events among elderly persons," N Engl J Med, 2005. 352(20): pp. 2049-60), albumin (Wang, T.J., et al., "Multiple biomarkers for the prediction of first major cardiovascular events and death," N Engl J Med, 2006. 355(25): pp. 2631-9), and various cytokines (Maletic, V. et al., "Neurobiology of depression: an integrated view of key findings," Int J Clin Pract, 2007. 61(12): pp. 2030-2040). The references listed above are herein incorporated by reference in their entirety. This example implementation may provide end-of-life care that can be personalized and dispensed based upon the analyses provided herein.

The terminally ill patient follows a certain illness trajectory when moving from health to ill health. This includes three stages: having a potentially curable illness, undergoing intensive treatment, and being diagnosed where no curative treatment exists. Often a patient is considered to be terminally ill when the life expectancy is estimated to be six months or less, under the assumption the disease will run its course. At each of these stages there is an age-dependent cognitive trajectory that is hypothesized as tractable. This trajectory may include depression, hopelessness, suicidal ideation, fear, anxiety, and anger. Treating these patients may fall into one of two approaches: palliative and hospice care.

The stress of having a terminal illness can lead to psychiatric disorders and need for mental health services. In one study, two-hundred and fifty-one pediatric patients with advanced cancer were studied for mental illness. Twelve percent met criteria of having Major Depressive Disorder, Generalized Anxiety Disorder, Panic Disorder, or Post-Traumatic Stress Disorder. Twenty-eight percent had access to mental health services, 17% used those services, and 90% responded that they would use mental health services if available (Kadan-Lottick, N. S., et al., "Psychiatric disorders and mental health service use in patients with advanced cancer: a report from the coping with cancer study," Cancer 2005. 104(12): pp. 2872-81, herein incorporated by reference in its entirety).

One area that appears to have no consideration to date is the application of computational linguistics to understand what terminal patients and parents (family members) are saying as death approaches and how this differs from the non care patients. This analysis relies on information extraction and natural language processing.

II.A. Information Extraction—Thought Markers

The goal of information extraction systems is to extract facts related to a particular domain from natural language texts. Texts that are inherently ambiguous, because of hyperbole or metaphors, often cause the accuracy of an information extraction system to decline. Information Extraction extracts data that are either nomothetic or idiographic. Nomothetic data represents statistical-type data, like age, gender, cholesterol levels, and so forth. Extracting information like the frequency of a rash occurring when a child is prescribed carbamazepine for epilepsy is a straightforward task as long as the nomothetic data are available. Ideographic data describe an individual's subjective characteristics like emotions, feelings, and so forth. Extracting information like the frequency of rash occurrences by an epileptic adolescent on carbamazepine is, on the other hand, not as straight forward.

Since the early 2000s there has been increased attention focused on ideographic information extraction. This focus has concentrated on topics like polarity (positive or negative) (Turney, P. and M. Littman, "Measuring praise and criticism: Inference of semantic orientation from association," ACM Transactions on Information Systems-TOIS, 2003. 21(4): pp. 315-346; and Dave, K. S. Lawrence, and D. Pennock, "Mining the peanut gallery: Opinion extraction and semantic classification of product reviews," 2003: ACM New York, N.Y., USA), hostility (Spertus, E., "Smokey: Automatic recognition of hostile messages. 1997: JOHN WILEY & SONS LTD.), multi-document summarization (Yu, H. and V. Hatzivassiloglou, "Towards answering opinion questions: Separating facts from opinions and identifying the polarity of opinion sentences," 2003), and tracking sentiments toward events (Tong. R., "An operational system for detecting and tracking opinions in on-line discussions. 2001; and Suh, E., E. Diener, and F. Fujita, "Events and subjective well-being: Only recent events matter," Journal of personality and social psychology, 1996, 70(5): pp. 1091-1102) and subsequently there have been hundreds of papers published on the subject (see above and Das, S. and M. Chen, "Yahoo! for Amazon: Sentiment extraction from small talk on the web," Management Science, 2007. 53(9): pp. 1375-1388). The references listed above are incorporated by reference in their entirety. Factors behind this interest include: the rise of machine learning methods in natural language processing and information retrieval; the availability of datasets for machine learning algorithms to be trained on, due to the blossoming of the World Wide Web and, specifically, the development of review-aggregation web-sites; and, of course realization of the fascinating intellectual challenges and commercial and intelligence applications. The present example implementation focuses on tracking sentiments about a major life event, in this case death.

II.B. BioMarkers

This example implementation may monitor, in an embodiment, a number of chemical based biomarkers. Each one has been shown to potentially change as death approaches. As discussed above, some biomarkers that may be related to tracking death are: C-reactive protein, NGal, cystatin C, albumin, and various cytokines.

A wide range of biomarkers, reflecting activity in a number of biological systems (e.g. neuroendocrine, immune, cardiovascular, and metabolic), have been found to prospectively predict disability, morbidity, and mortality in older adult populations. For example, Clarke, et al identified a correlation between biomarkers of inflammation (C-reactive protein, fibrinogen and total/HDL-C) and vascular and non-vascular mortality in older men. Shlipak, et al. showed that higher cystatin C levels were directly associated, in a dose-response manner, with a higher risk of death from all causes. Gruenewald, et al studied 13 different biomarkers in the elderly over a 12 year period (n=1189). Using recursive partitioning methods they found that most all were associated with high-risk pathways and combinations of biomarkers were associated with mortality. Wang, et al measured 10 biomarkers in 3209 patients attending routine examination cycle of the Framingham Heart study for the prediction of the first major cardiovascular events and death. They found that using the 10 contemporary biomarkers adds only moderately to standard risk factors. Finally, Zethelius, et al. studied the incremental usefulness of adding multiple biomarkers from different disease pathways for predicting the risk of cardiovascular death. They found that the simultaneous addition of several biomarkers improves the risk stratification for death from cardiovascular causes. Additionally, some of these cytokines have been linked to major mood disorders and suicidal and non-suicidal tendencies (TNF a, IL-6, and IL-10).

The present example implementation provides a system and method that integrates biomarkers and thought-marker analysis to result in a better understanding how to increase the quality of care for terminally ill patients.

Figure 6:
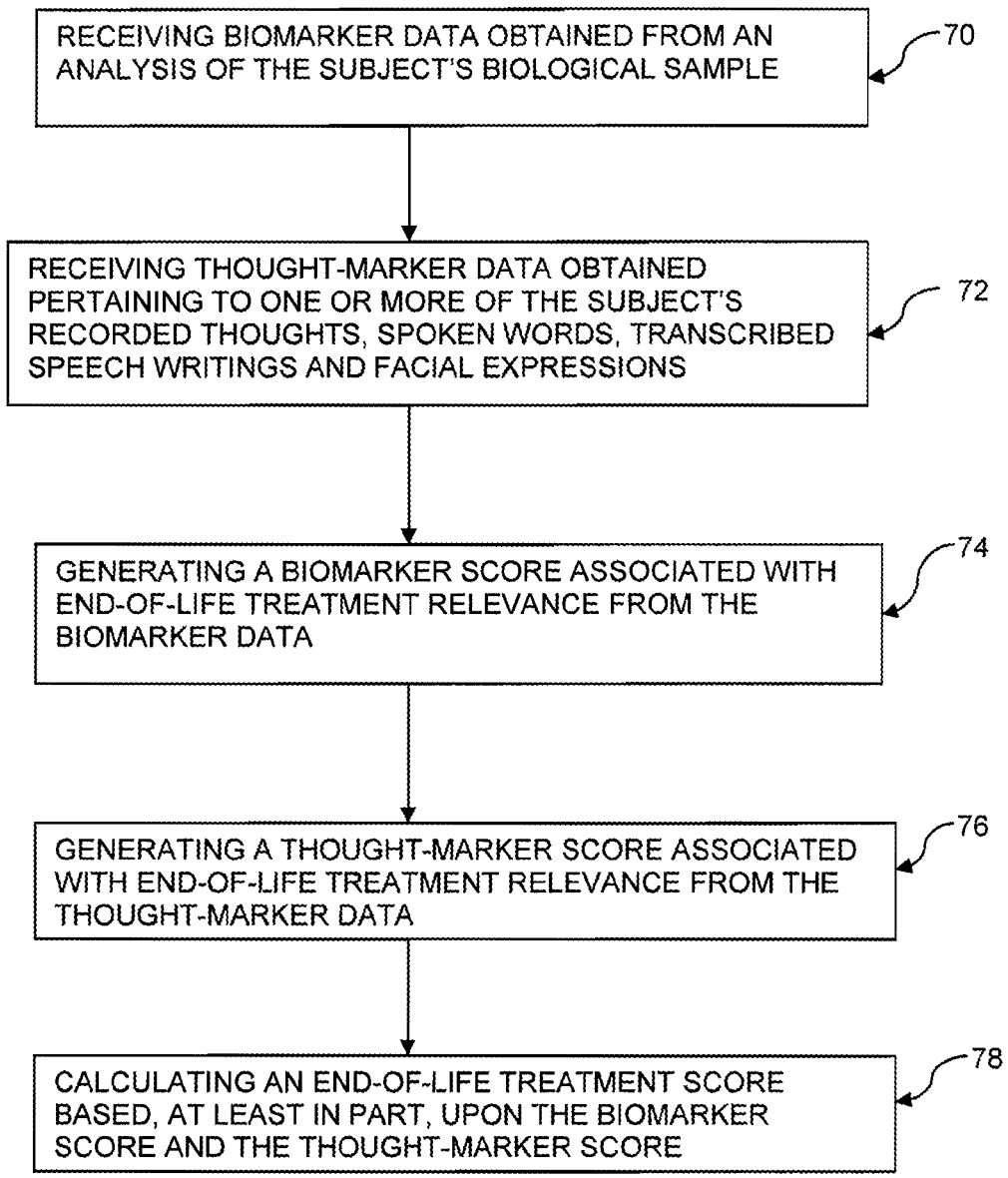
FIG. 6. is a flow diagram depicting another exemplary embodiment of the present invention.

FIG. 6 provides a flow diagram representing an embodiment of a method according to the present exemplary implementation. This method may be operating from one or more memory devices including computer-readable instructions configured to instruct a computerized system to perform the method, and the method may be operating on a computerized system including one or more computer servers (or other available devices) accessible over a computer network such as the Internet or over some other data network. The method may include the following operations, which do not necessarily need to be performed in the stated order. Operation 70 involves receiving biomarker data obtained from an analysis of a subject's biological sample. Operation 72 involves receiving thought-marker data obtained pertaining to one or more of the subject's recorded thoughts, spoken words, transcribed speech, writings and/or facial expressions. Operation 74 involves generating a biomarker score associated with end-of-life treatment relevance from the biomarker data. Operation 76 involves generating a thought-marker score associated with end-of-life treatment relevance from the thought-marker data. Operation 78 involves calculating an end-of-life treatment score based, at least in part, upon the biomarker score and the thought-marker score.

In an embodiment, the step of generating the biomarker score may include a step of accessing a level of one or more chemical based biomarkers from the biological sample that have been shown to change as the subject nears death. Alternatively, or in addition, the step of generating the biomarker score includes a step of assessing a level of C-reactive protein, NGal, cystatin, albumin, IL-6 cytokine, IL-2 cytokine, IFN-γ cytokine, IL-4 cytokine and/or TGF-β1 cytokine biomarkers from the biological sample.

In an embodiment, the step of generating a thought-marker score includes a step of determining a correlation between (a) the one or more of the human subject's recorded thoughts, spoken words, transcribed speech, writings and facial expressions; and (b) a corpus of thought data collected pertaining, at least in part, to the end-of-life treatment relevance.

In an embodiment, the step of generating a biomarker score includes a step of calculating a composite score related to two or more biological markers associated with the end-of-life treatment relevance from the biomarker data.

In an embodiment, the step of calculating the end-of-life treatment score includes steps of: (a) normalizing the biomarker score, (b) normalizing the thought-marker scores, and (c) calculating a mean of at least the normalized biomarker score and the thought-marker scores. Furthermore, these normalizing steps may normalize between a scale of 0.0 and 1.0 and/or a scale of 0 and $10^N$ where N is an integer (e.g. between 0 and 10, between 0 and 100, between 0 and 1,000 and so forth).

III. Assessment of Neuropsychiatric Conditions

Based upon the above, it will be readily apparent that many neuropsychiatric conditions may be readily assessed based upon the implementation of the methodologies and systems provided herein. Examples of such other neuropsychiatric conditions may include, without limitation: a risk that a subject may perform or repeat a criminal act and/or a harmful act, a risk of the subject having a psychiatric illness (such as schizophrenia), and a risk of a subject feigning a psychiatric illness.

Figure 7:
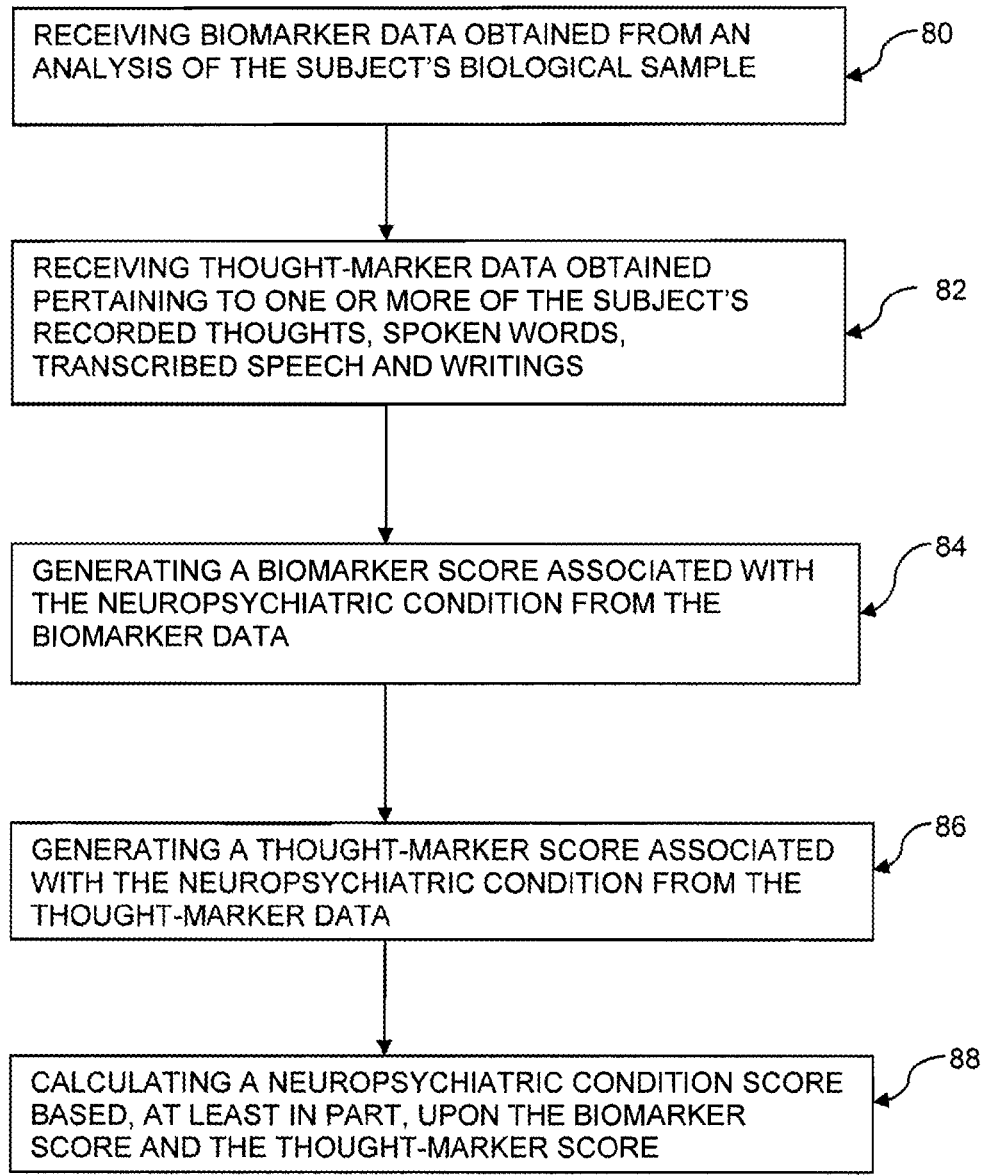
FIG. 7 is a flow diagram depicting another exemplary embodiment of the present invention.

Such a method for assessing such neuropsychiatric conditions may be operating from one or more memory devices including computer-readable instructions configured to instruct a computerized system to perform the method, and the method may be operating on a computerized system including one or more computer servers (or other available devices) accessible over a computer network such as the Internet or over some other data network. The method may include the following operations as shown in FIG. 7, which do not necessarily need to be performed in the stated order. Such operations may include an operation 80 of receiving biomarker data associated from an analysis of the subject's biological sample. An operation 82 may involve receiving thought-marker data obtained pertaining to one or more of the subject's recorded thoughts, spoken words, transcribed speech, and writings. An operation 84 may include generating a biomarker score associated with the neuropsychiatric condition from the biomarker data. An operation 86 may include generating a thought-marker score associated with the neuropsychiatric condition from the thought-marker data. An operation 88 may involve calculating a neuropsychiatric condition score based, at least in part, upon the biomarker score and the thought-marker score.

In an embodiment, the step of generating the biomarker score may include a step of assessing a level of at least a cytokine, a metabolite, a polymorphism, a genotype, a polypeptide, and an mRNA of the human subject. For example, the step of generating the biomarker score may include a step of assessing a level of a hydroxyindoleaceticacid (5HIAA).

In an embodiment, the step of generating a thought-marker score includes a step of determining a correlation between (a) the human subject's recorded thoughts, spoken words, transcribed speech and/or writings; and (b) a corpus of thought data collected pertaining, at least in part, to the neuropsychiatric condition. Further, this correlation may be determined, at least in part, utilizing natural language processing and/or machine learning algorithms.

In an embodiment, the method may further include a step of receiving clinical data of the subject associated with the neuropsychiatric condition; may include a step of generating a clinical data score from the clinical data; and the step of calculating in neuropsychiatric condition score may be based, at least in further part, upon the clinical data score. Further, the clinical data of the subject associated with the neuropsychiatric condition may include at least a portion of medical patient record data associated with the subject; may include demographic data associated with the subject; and/or may include interview and/or survey data obtained from the subject. With this embodiment, it is possible that the step of calculating a neuropsychiatric condition score may include steps of (a) normalizing the biomarker score, (b) normalizing the thought-marker score, (c) normalizing the clinical data score and (d) calculating a mean of at least the normalized biomarker, thought marker and clinical data scores. Further, the normalizing steps normalize between a numerical scale of 0.0 to 1.0 and/or a scale of 0 and $10^N$, wherein N is an integer. Further, the step of generating a clinical data score may include a step of calculating a percentage of risks associated with the neuropsychiatric condition from the subject compared to a predetermined set of risks associated with the neuropsychiatric condition.

In an embodiment, the step of generating a biomarker score includes a step of calculating a composite score related to two or more biological markers associated with the neuropsychiatric condition from the biomarker data.

In an embodiment, the step of calculating a neuropsychiatric condition score includes steps of (a) normalizing the biomarker score, (b) normalizing the thought marker score and (c) calculating a mean of at least the normalized biomarker and the thought marker scores.

In an embodiment, the method further includes a step of automatically recommending, based upon the calculated neuropsychiatric condition score, a subject's treatment regimen, a subject's counseling session, a subject's intervention program and/or a subject's care program.

Following from the above disclosure, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. One or more non-transitory computer readable memory devices including computer-readable instructions configured to instruct a computerized system to perform a method for assessing a suicide attempt risk of a human subject, the method including the steps of:

obtaining a biological sample from the subject;

determining one or more suicide risk associated biological markers by a method comprising one or more of a polymerase chain reaction (PCR), a reverse transcription PCR reaction (RT-PCR), mass spectroscopy (MS), high pressure liquid chromatography (HPLC), LC-MS, DNA sequencing, and an enzyme-linked, bead based, or sandwich immunoassay to provide biomarker data for the subject;

receiving, using one or more processors, the biomarker data;

receiving, using one or more processors, thought-marker data including one or more of the subject's recorded thoughts, spoken words, transcribed speech, and writings;

generating, using one or more processors, a numerical biomarker score from the biomarker data, said biomarker score generated by normalizing, using the one or more processors, the one or more determined suicide risk associated biological markers, generating a normalized score for each of the markers based on the strength of the marker's association with suicide risk and summing the individual normalized scores for the one or more determined suicide risk associated biological markers;

generating, using one or more processors, a thought-marker score associated with the suicide attempt risk from the thought-marker data by a method comprising the steps of determining a correlation between (a) the thought marker data of the subject and (b) a corpus of thought data comprising a set of suicide notes language associated with prior completions of suicides, the correlation determined using a machine learning method implementing a classification algorithm selected from the group consisting of decision trees, classification rules, function models, and instance-based learner methods, the machine learning method comprising extracting and quantifying relevant content features of the thought marker data and creating a heterogeneous, multidimensional feature space, normalizing the feature values, and generating the thought-marker score based upon the strength of the correlation, and generating a suicide attempt risk score based, at least in part, upon the biomarker score and the thought-marker score, and generating, using the suicide attempt risk score, a treatment program for the subject.

2. The one or more non-transitory computer readable memory devices of claim 1, wherein the method's step of determining one or more suicide risk associated biological markers includes a step of determining a level of a hydroxy-indoleacetic acid (5HIAA).

3. The one or more non-transitory computer readable memory devices of claim 1, wherein the method's step of determining one or more suicide risk associated biological markers includes a step of determining the presence of the S and L alleles of the 5' upstream regulatory region of the serotonin transporter gene (5-HTTLPR).

4. The one or more non-transitory computer readable memory devices of claim 1, wherein the method's step of determining one or more suicide risk associated biological markers includes a step of determining the presence of one or more single nucleotide polymorphisms taken from a group consisting of: A218C of the TPH1 gene, A779C of the TPH1 gene, and A59G of the SLC6A3 gene.

5. The one or more non-transitory computer readable memory devices of claim 1, wherein the method's step of determining one or more suicide risk associated biological markers includes a step of determining an mRNA level of 5-HT(2A) mRNA.

6. The one or more non-transitory computer readable memory devices of claim 1, wherein the method's step of determining one or more suicide risk associated biological markers includes a step of determining a level of one or more cytokines taken from a group consisting of: IL-6, IL-2, IFN-γ, IL-4 and TGF-β1.

7. The one or more non-transitory computer readable memory devices of claim 1, wherein the method's step of determining one or more suicide risk associated biological markers includes a step of determining a level of serotonin (5-HT).

8. The one or more non-transitory computer readable memory devices of claim 1, wherein the method further includes:

a step of receiving clinical data of the subject associated with the suicide attempt risk and a step of generating a clinical data score from the clinical data, and the method's step of calculating a suicide attempt risk score is based, at least in further part, upon the clinical data score.

9. The one or more non-transitory computer readable memory devices of claim 8, wherein the clinical data of the subject associated with the suicide risk includes data pertaining to previous suicide attempts by the subject.

10. The one or more non-transitory computer readable memory devices of claim 9, wherein the clinical data of the subject associated with the suicide risk includes further includes one or more of, data pertaining to a level of interpersonal discord, data pertaining to a presence of a mood disorder, data pertaining to a history of substance use, data pertaining to a history of impulsive aggression, data pertaining to a family history of suicidal behavior, data pertaining to access to weapons such as firearms, and data pertaining to recent psychosocial stressors.

11. The one or more non-transitory computer readable memory devices of claim 8, wherein the method's step of calculating a suicide risk score includes steps of:
- normalizing the biomarker score;
- normalizing the thought-marker score;
- normalizing the clinical data score; and
- calculating a mean of at least the normalized biomarker, thought-marker and clinical data scores.

12. The one or more non-transitory computer readable memory devices of claim 11, wherein the method's normalizing steps, normalize between at least one of the following numerical scales: (a) 0.0 and 1.0, and (b) 0.0 and $10^N$, where N is an integer.

13. The one or more non-transitory computer readable memory devices of claim 8, wherein the method's step of generating a clinical data score includes a step of calculating a percentage of risks associated with the suicide risk from the subject compared to a predetermined set of risks associated with the suicide risk.

14. The one or more non-transitory computer readable memory devices of claim 1, wherein the method's step of generating a biomarker score includes a step of calculating a composite score related to two or more biological markers associated with the suicide risk from the biomarker data.

15. The one or more non-transitory computer readable memory devices of claim 1, wherein the method's step of calculating a suicide risk score includes steps of:
- normalizing the biomarker score;
- normalizing the thought-marker score;
- calculating a mean of at least the normalized biomarker and the thought-marker scores.

16. The one or more non-transitory computer readable memory devices of claim 15, wherein the method's normalizing steps, normalize between at least one of the following numerical scales: (a) 0.0 and 1.0, and (b) 0.0 and $10^N$, where N is an integer.

17. One or more non-transitory computer readable memory devices including computer-readable instructions configured to instruct a computerized system to perform a method for assessing a suicide attempt risk of a human subject, the method including the steps of:
- obtaining a biological sample from the subject;
- determining one or more suicide risk associated biological markers based on the obtained biological sample by a method comprising one or more of a polymerase chain reaction (PCR), a reverse transcription PCR reaction (RT-PCR), mass spectroscopy (MS), high pressure liquid chromatography (HPLC), LC-MS, DNA sequencing, and an enzyme-linked, bead based, or sandwich immunoassay;
- normalizing, using one or more processors, the one or more determined suicide risk associated biological markers and generating a normalized score for each based on the strength of marker's association with suicide risk;
- generating, using the one or more processors, a biomarker score based on a sum of individual normalized scores for the one or more determined suicide risk associated biological markers;
- receiving, using the one or more processors, one or more thought markers of the subject, the one or more thought markers including one or more of the subject's recorded thoughts, spoken words, transcribed speech, and writings;
- executing, using the one or more processors, a first query and transmitting the first query to a suicide notes database to obtain a plurality of suicide notes associated with prior completions of suicides, the one or more processors being communicatively coupled to the suicide notes database using one or more communications networks;
- comparing, using one or more machine learning methods, the one or more thought markers and the obtained plurality of suicide notes to determine a correlation between (a) the one or more thought markers of the subject and (b) the obtained plurality of suicide notes, the one or more machine learning methods implementing a classification algorithm including at least one of the following: a decision tree, a classification rule, a function model, an instance-based learner method, and any combination thereof,
  - the one or more machine learning methods including
    - extracting and quantifying relevant content features of the one or more thought markers; and
    - generating, based on extracting and quantifying, a heterogeneous, multidimensional feature space containing a plurality of feature values corresponding to quantified content features;
    - normalizing the generated feature values; and
  - generating, using the normalized generated feature values, a thought-marker score based upon a strength of the correlation, and
- generating a suicide attempt risk score based on a combination of the biomarker score and the thought-marker score; and
- generating, using the suicide attempt risk score, a treatment program for the subject.

* * * * *